US012788729B2

(12) United States Patent
Lee et al.

(10) Patent No.: US 12,788,729 B2
(45) Date of Patent: Nov. 10, 2026

(54) AMISELIMOD FOR PREVENTING, TREATING OR AMELIORATING ULCERATIVE COLITIS

(71) Applicant: Bausch Health Ireland Limited, Dublin (IE)

(72) Inventors: Jimin Lee, Bridgewater, NJ (US); Neal Slatkin, Bridgewater, NJ (US); Ezra R. Lowe, Morristown, NJ (US); Zeev Heimanson, Bridgewater, NJ (US)

(73) Assignee: Bausch Health Ireland Limited, Dublin (IE)

( * ) Notice: Subject to any disclaimer, the term of this patent is extended or adjusted under 35 U.S.C. 154(b) by 469 days.

(21) Appl. No.: 18/276,120

(22) PCT Filed: Feb. 8, 2022

(86) PCT No.: PCT/EP2022/053030

§ 371 (c)(1), (2) Date: Aug. 7, 2023

(87) PCT Pub. No.: WO2022/167690

PCT Pub. Date: Aug. 11, 2022

(65) Prior Publication Data

US 2024/0299318 A1 Sep. 12, 2024

Related U.S. Application Data

(60) Provisional application No. 63/147,060, filed on Feb. 8, 2021.

(51) Int. Cl.
*A61K 31/137* (2006.01)

(52) U.S. Cl.
CPC .................................. *A61K 31/137* (2013.01)

(58) Field of Classification Search
CPC ........... A61K 31/137; A61P 1/04; A61P 37/00
See application file for complete search history.

(56) References Cited

U.S. PATENT DOCUMENTS

| | | | |
|---|---|---|---|
| 8,492,441 | B2 | 7/2013 | Legangneux |
| 8,809,304 | B2 | 8/2014 | Kiuchi et al. |
| 2018/0369212 | A1 | 12/2018 | Rabbani et al. |
| 2020/0017510 | A1 | 1/2020 | Ammann et al. |

FOREIGN PATENT DOCUMENTS

| | | | | |
|---|---|---|---|---|
| JP | 2017533895 | A | 11/2017 | |
| JP | 2018527406 | A | 9/2018 | |
| WO | 2016051188 | A1 | 4/2016 | |
| WO | WO-2016112075 | A1 * | 7/2016 | A61P 37/02 |
| WO | 2017024355 | A1 | 2/2017 | |
| WO | 2020051568 | A1 | 3/2020 | |
| WO | 2021021735 | A1 | 2/2021 | |

OTHER PUBLICATIONS

Danese et al., J. of Crohn's and Colitis, publ. 2018, pp. S678-S686 (Year: 2018).*

Abbass, et al., "Adalimumab for induction of remission in Crohn's disease (Review)", Cochrane Database of Systematic Reviews, Issue 11, Article No. CD012878, 2019, pp. 1-29.

"Extension Study of MT-1303 in Subjects with Crohn's Disease", Retrieved from the Internet: URL:https://clinicaltrials.gov/ct2/show/record/NCT02389790?view=record, retrieved on May 30, 2022, 2017, 5 pages.

"Safety and Efficacy of MT-1303 in Subjects with Moderate to Severe Active Crohn's Disease", Retrieved from the Internet: URL:https://clinicaltrials.gov/ct2/show/NCT02378688, retrieved on May 30, 2022, 2016, 6 pages.

"Study Evaluating Efficacy and Safety of Amiselimod (MT-1303) in Mild to Moderate Ulcerative Colitis", Retrieved from Internet: URL:https://clinicaltrials.gov/ct2/show/NCT04857112, retrieved on May 30, 2022, 2021.

D'Haens , et al., "A Phase II, Multicentre, Randomised, Double-Blind, Placebo-controlled Study to Evaluate Safety, Tolerability, and Efficacy of Amiselimod in Patients with Moderate to Severe Active Crohn's Disease", Journal of Crohn's and Colitis, Oxford University Press, NLD, No. Corrected Proof, 2021, pp. 1-10.

Harada , et al., "Cardiac effects of amiselimod compared with fingolimod and placebo: results of a randomised, parallel-group, phase I study in healthy subjects", Br J Clin Pharmacol, 83, 2017, pp. 1011-1027.

Shimano , et al., "Amiselimod (MT-1303), a novel sphingosine 1-phosphate receptor-1 functional antagonist, inhibits progress of chronic colitis induced by transfer of CD4(+)CD45RB(high) T cells", PLOS One, vol. 14, No. 12, 2019, 12 pages.

Sugahara , et al., "Amiselimod, a novel sphingosine 1-phosphate receptor-1 modulator, has potent therapeutic efficacy for autoimmune diseases, with low bradycardia risk", Br J Pharmacol, 174, 2017, pp. 15-27.

PCT International Search Report & Written Opinion dated Jun. 10, 2022 for corresponding PCT International Application No. PCT/EP2022/053030.

"Velsipity(TM) Etrasimod FDA Prescribing Information," retrieved from internet on Jun. 4, 2026, https://www.accessdata.fda.gov/drugsatfda_docs/label/2024/216956s001lbl.pdf, Revised Jun. 2024, pp. 1-28.

* cited by examiner

*Primary Examiner* — Sarah Pihonak

(74) *Attorney, Agent, or Firm* — Saul Ewing LLP; Domingos J. Silva; Dennis Ostrovsky

(57) ABSTRACT

Described herein are methods for treating, ameliorating, and/or preventing ulcerative colitis (UC) as well as other inflammatory gastrointestinal disorders using amiselimod. The method of treatment includes dosing amiselimod at a larger initial dose as compared to the eventual maintenance dose.

39 Claims, 3 Drawing Sheets

AMISELIMOD FOR PREVENTING, TREATING OR AMELIORATING ULCERATIVE COLITIS

CROSS-REFERENCE TO RELATED APPLICATION

This application is a 35 U.S.C. § 371 national phase application of, and claims priority to, International Application No. PCT/EP2022/053030, filed Feb. 8, 2022, which claims priority under 35 U.S.C. § 119(e) to U.S. Provisional Patent Application No. 63/147,060, entitled "METHOD OF TREATING OR AMELIORATING ULCERATIVE COLITIS," filed Feb. 8, 2021, the disclosures of all of which are incorporated herein by reference in their entireties.

BACKGROUND

Ulcerative colitis (UC) is a chronic, idiopathic inflammatory disease that affects the colon. It has a bimodal pattern of incidence, with main onset in patients between 15 and 30 years of age and a second smaller peak between 50 and 70 years of age. It is characterized by relapsing and remitting inflammation characteristically restricted to the mucosal surface. Disease distribution is stratified by the extent of colonic involvement, from proctitis to left-sided colitis or extensive colitis (pancolitis). The incidence and prevalence of ulcerative colitis have been increasing over time worldwide.

There remains an unmet need for safe and effective treatments of UC and other disorders of the gastrointestinal tract. The present disclosure solves this need.

BRIEF SUMMARY OF THE INVENTION

Methods of preventing, treating, and/or ameliorating ulcerative colitis and/or inflammation in the gastrointestinal tract of a subject in need thereof are provided.

In certain embodiments, the method includes: administering to the subject a first dose of amiselimod, or a pharmaceutically acceptable salt or enantiomer thereof, during a first administration period; and administering to the subject a second dose of amiselimod, or a pharmaceutically acceptable salt or enantiomer thereof, during a second administration period, wherein the first dose is larger than the second dose.

In certain embodiments, the method includes: administering to the subject a therapeutically effective first dose of amiselimod, or a pharmaceutically acceptable salt or enantiomer thereof, during a first administration period; and administering to the subject a therapeutically effective second dose of amiselimod, or a pharmaceutically acceptable salt or enantiomer thereof, during a second administration period, wherein the first dose is larger than the second dose.

In certain embodiments, this disclosure includes a method of treating or ameliorating ulcerative colitis in subject in need thereof comprising the steps of administering to the subject a first dose of a composition comprising amiselimod during a first administration period; and administering to the subject a second dose of a composition comprising amiselimod during a second administration period, wherein the first dose is larger than the second dose.

In certain embodiments, this disclosure includes a method of treating or ameliorating ulcerative colitis in subject in need thereof comprising the steps of administering to the subject a first dose of amiselimod or a pharmaceutically acceptable salt thereof during a first administration period; and administering to the subject a second dose of amiselimod or a pharmaceutically acceptable salt thereof during a second administration period, wherein the first dose is larger than the second dose.

In certain embodiments, this disclosure includes a method of treating or ameliorating ulcerative colitis in subject in need thereof comprising the steps of administering to the subject a therapeutically effective first dose of amiselimod during a first administration period; and administering to the subject a therapeutically effective second dose of amiselimod during a second administration period, wherein the first dose is larger than the second dose.

In certain embodiments, this disclosure includes a method of treating mild to moderate ulcerative colitis in subject in need thereof comprising the steps of administering to the subject a first dose of a composition comprising amiselimod during a first administration period; and administering to the subject a second dose of a composition comprising amiselimod during a second administration period, wherein the first dose is larger than the second dose.

In certain embodiments, this disclosure includes a method of treating mild to moderate ulcerative colitis in subject in need thereof comprising the steps of administering to the subject a first dose of amiselimod or a pharmaceutically acceptable salt thereof during a first administration period; and administering to the subject a second dose of amiselimod or a pharmaceutically acceptable salt thereof during a second administration period, wherein the first dose is larger than the second dose.

In certain embodiments, this disclosure includes a method of treating mild to moderate ulcerative colitis in subject in need thereof comprising the steps of administering to the subject a therapeutically effective first dose of amiselimod during a first administration period; and administering to the subject a therapeutically effective second dose of amiselimod during a second administration period, wherein the first dose is larger than the second dose.

In certain embodiments, this disclosure includes a method of treating or ameliorating inflammation in the gastrointestinal tract in subject in need thereof comprising the steps of administering to the subject a first dose of a composition comprising amiselimod during a first administration period; and administering to the subject a second dose of a composition comprising amiselimod during a second administration period, wherein the first dose is larger than the second dose.

In certain embodiments, this disclosure includes a method of treating or ameliorating inflammation in the gastrointestinal tract in subject in need thereof comprising the steps of administering to the subject a first dose of amiselimod or a pharmaceutically acceptable salt thereof during a first administration period; and administering to the subject a second dose of amiselimod or a pharmaceutically acceptable salt thereof during a second administration period, wherein the first dose is larger than the second dose.

In certain embodiments, this disclosure includes a method of treating or ameliorating inflammation in the gastrointestinal tract in subject in need thereof comprising the steps of administering to the subject a therapeutically effective first dose of amiselimod during a first administration period; and administering to the subject a therapeutically effective second dose of amiselimod during a second administration period, wherein the first dose is larger than the second dose.

In some embodiments of the foregoing methods, administration of the first dose to the subject does not induce a negative chronotropic effect in the subject.

In some embodiments of the foregoing methods, the first dose is about 1.5 to about 2.5 times larger than the second dose.

In some embodiments of the foregoing methods, administration of the first dose comprises administration of about 0.05 mg to about 10 mg of amiselimod.

In some embodiments of the foregoing methods, administration of the second dose comprises administration of about 0.05 mg to about 10 mg of amiselimod.

In some embodiments of the foregoing methods, administration of the first dose comprises administration of about 0.1 mg to about 1 mg of amiselimod.

In some embodiments of the foregoing methods, administration of the second dose comprises administration of about 0.1 mg to about 1 mg of amiselimod.

In some embodiments of the foregoing methods, administration of the first dose comprises administration of at least about 0.1, 0.2, 0.3, 0.4, 0.5, 0.6, 0.7, 0.8, 0.9, or about 1.0 mg of amiselimod. In some embodiments of the foregoing methods, administration of the first dose comprises administration of less than about 0.1, 0.2, 0.3, 0.4, 0.5, 0.6, 0.7, 0.8, 0.9, or about 1.0 mg of amiselimod. In some embodiments of the foregoing methods, administration of the first dose comprises administration of about 0.1, 0.2, 0.3, 0.4, 0.5, 0.6, 0.7, 0.8, 0.9, or about 1.0 mg of amiselimod.

In some embodiments of the foregoing methods, administration of the first dose comprises administration of about 0.8 mg of amiselimod. In some embodiments of the foregoing methods, administration of the first dose comprises administration of about 0.4 mg of amiselimod.

In some embodiments of the foregoing methods, administration of the second dose comprises administration of about 0.4 mg of amiselimod. In some embodiments of the foregoing methods, administration of the second dose comprises administration of about 0.2 mg of amiselimod.

In some embodiments of the foregoing methods, administration of the first and second doses comprise, independently, administration of one or more unit doses.

In some embodiments of the foregoing methods, administration of the first dose comprises administration of about 0.05 mg to about 10 mg of amiselimod per unit dose.

In some embodiments of the foregoing methods, administration of the second dose comprises administration of about 0.05 mg to about 10 mg of amiselimod per unit dose.

In some embodiments of the foregoing methods, administration of the first dose comprises administration of about 0.1 mg to about 1 mg of amiselimod per unit dose.

In some embodiments of the foregoing methods, administration of the second dose comprises administration of about 0.1 mg to about 1 mg of amiselimod per unit dose.

In some embodiments of the foregoing methods, administration of the first dose comprises administration of at least about 0.1, 0.2, 0.3, 0.4, 0.5, 0.6, 0.7, 0.8, 0.9, or about 1.0 mg of amiselimod per unit dose. In some embodiments of the foregoing methods, administration of the first dose comprises administration of less than about 0.1, 0.2, 0.3, 0.4, 0.5, 0.6, 0.7, 0.8, 0.9, or about 1.0 mg of amiselimod per unit dose. In some embodiments of the foregoing methods, administration of the first dose comprises administration of about 0.1, 0.2, 0.3, 0.4, 0.5, 0.6, 0.7, 0.8, 0.9, or about 1.0 mg of amiselimod per unit dose.

In some embodiments of the foregoing methods, administration of the first dose comprises administration of about 0.8 mg of amiselimod per unit dose. In some embodiments of the foregoing methods, administration of the first dose comprises administration of about 0.4 mg of amiselimod per unit dose.

In some embodiments of the foregoing methods, administration of the second dose comprises administration of about 0.4 mg of amiselimod per unit dose. In some embodiments of the foregoing methods, administration of the second dose comprises administration of about 0.2 mg of amiselimod per unit dose.

In some embodiments of the foregoing methods, administration of the first and second doses comprise, independently, administration of daily doses of amiselimod.

In some embodiments of the foregoing methods, administration of the first dose comprises administration of about 0.05 mg to about 10 mg of amiselimod per daily dose.

In some embodiments of the foregoing methods, administration of the second dose comprises administration of about 0.05 mg to about 10 mg of amiselimod per daily dose.

In some embodiments of the foregoing methods, administration of the first dose comprises administration of about 0.1 mg to about 1 mg of amiselimod per daily dose.

In some embodiments of the foregoing methods, administration of the second dose comprises administration of about 0.1 mg to about 1 mg of amiselimod per daily dose.

In some embodiments of the foregoing methods, administration of the first dose comprises administration of at least about 0.1, 0.2, 0.3, 0.4, 0.5, 0.6, 0.7, 0.8, 0.9, or about 1.0 mg of amiselimod per daily dose. In some embodiments of the foregoing methods, administration of the first dose comprises administration of less than about 0.1, 0.2, 0.3, 0.4, 0.5, 0.6, 0.7, 0.8, 0.9, or about 1.0 mg of amiselimod per daily dose. In some embodiments of the foregoing methods, administration of the first dose comprises administration of about 0.1, 0.2, 0.3, 0.4, 0.5, 0.6, 0.7, 0.8, 0.9, or about 1.0 mg of amiselimod per daily dose.

In some embodiments of the foregoing methods, administration of the first dose comprises administration of about 0.8 mg of amiselimod per daily dose. In some embodiments of the foregoing methods, administration of the first dose comprises administration of about 0.4 mg of amiselimod per daily dose.

In some embodiments of the foregoing methods, administration of the second dose comprises administration of about 0.4 mg of amiselimod per daily dose. In some embodiments of the foregoing methods, administration of the second dose comprises administration of about 0.2 mg of amiselimod per daily dose.

BRIEF DESCRIPTION OF THE FIGURES

The drawings illustrate generally, by way of example, but not by way of limitation, various embodiments of the present application.

DETAILED DESCRIPTION OF THE INVENTION

Figure 1:
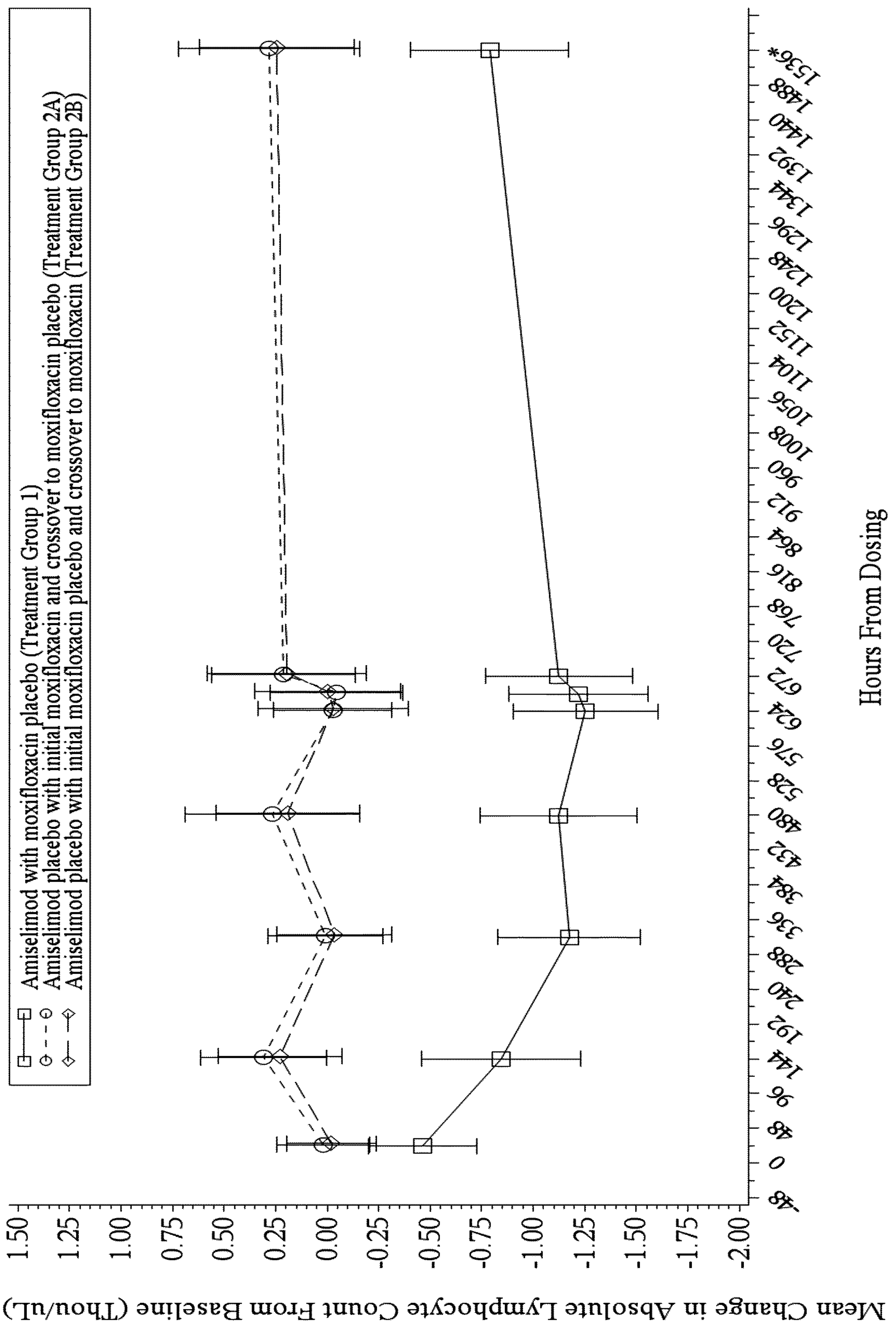
FIG. 1 shows an arithmetic mean (standard deviation) change in absolute lymphocyte counts from baseline (Thou/μL) vs time for treatment in a Phase 1 clinical study.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

Definitions

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "efficacy" refers to the maximal effect (Emax) achieved within an assay.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids or bases, including inorganic acids or bases, organic acids or bases, solvates, hydrates, or clathrates thereof. For example, a pharmaceutically acceptable salt may be a hydrochloride salt.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds described herein include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "pharmaceutically acceptable carrier" or "pharmaceutically acceptable excipient" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound described herein within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound(s) described herein, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound(s) described herein, and are physiologically acceptable to the patient. Supplementary active compounds may also be incorporated into the compositions. The "pharmaceutically acceptable carrier" may further include a pharmaceutically acceptable salt of the compound(s) described herein. Other additional ingredients that may be included in the pharmaceutical compositions used with the methods or compounds described herein are known in the art and described, for example in Remington's Pharmaceutical Sciences (Genaro, Ed., Mack Publishing Co., 1985, Easton, PA), which is incorporated herein by reference.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "potency" refers to the dose needed to produce half the maximal response ($ED_{50}$).

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound or compounds as described herein (alone or in combination with another pharmaceutical agent), to a patient, or application or administration of a therapeutic agent to an isolated tissue or cell line from a patient (e.g., for diagnosis or ex vivo applications), who has a condition contemplated herein or a symptom of a condition contemplated herein, with the purpose to cure, heal, alleviate, relieve, alter, remedy, ameliorate, improve or affect a condition contemplated herein, or the symptoms of a condition contemplated herein. Such treatments may be specifically tailored or modified, based on knowledge obtained from the field of pharmacogenomics.

As used herein, the terms "modulate" and "modulation" refer to a change in biological activity for a biological molecule (e.g., a protein, gene, peptide, antibody, and the like), where such change may relate to an increase in biological activity (e.g., increased activity, agonism, activation, expression, upregulation, and/or increased expression) or decrease in biological activity (e.g., decreased activity, antagonism, suppression, deactivation, downregulation, and/or decreased expression) for the biological molecule.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

Compositions

In some embodiments, this disclosure described herein refers to methods of administering the compound amiselimod (MT-1303) and/or compositions comprising the same. Amiselimod is an orally available selective S1P receptor modulator. Amiselimod, in free base form, is shown in Formula I.

(I)

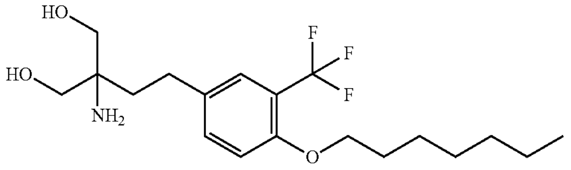

In some embodiments, and where applicable, the term amiselimod encompasses both the free base and pharmaceutically acceptable salts thereof (e.g., amiselimod hydrochloride). Amiselimod is described, for example, in U.S. Pat. No. 8,809,304, the entirety of which is incorporated herein by reference.

Amiselimod is effectively converted in vivo into its active metabolite, the (S)-enantiomer of MT-1303-P ((S)-MT-1303-P) shown in Formula II.

(II)

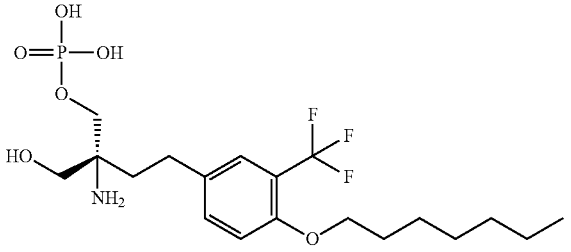

(S)-MT-1303-P (S)-MT-1303-P is a highly selective $S1P_1$ receptor agonist. (S)-MT-1303-P showed an agonistic activity at human $S1P_1$ receptor more potently than at human $S1P_4$ receptor and human S1Ps receptor and showed no agonistic activity at human $S1P_2$ receptor or $S1P_3$ receptor. The long half-life (approximately 400 hours in humans) of amiselimod and MT-1303-P indicates that both will slowly accumulate to steady state over a period of about 10 weeks.

Amiselimod at an oral dose of 0.1 mg/kg or higher significantly reduced the number of peripheral blood lymphocytes (PBLs) in mice, rats, and cynomolgus monkeys. The reduction in peripheral lymphocyte counts following MT-1303 administration is postulated to be due to inhibition of $S1P_1$ receptor-dependent lymphocyte egress from secondary lymphoid organs by induction of lymphocytic $S1P_1$ receptor internalization. Oral administration of amiselimod reduced colitis in the adoptive transfer of $CD4^{+}CD45RB^{high}$ T cells in SCID mice, and amiselimod's effect was comparable to that of a murine anti-tumor necrosis factor-α (TNF-α) antibody in this model.

In some embodiments, compositions described herein refer to compositions that include amiselimod and a pharmaceutically acceptable excipient.

In some embodiments, compositions described herein include amiselimod, and/or a pharmaceutically acceptable salt thereof, and a pharmaceutically acceptable excipient.

In some embodiments, compositions described herein include a pharmaceutically acceptable salt of amiselimod and a pharmaceutically acceptable excipient.

In some embodiments, compositions described herein include a therapeutically effective amount amiselimod, and/or a pharmaceutically acceptable salt thereof, and a pharmaceutically acceptable excipient. In some embodiments, compositions described herein include a therapeutically effective amount of a pharmaceutically acceptable salt of amiselimod and a pharmaceutically acceptable excipient.

The compositions containing the compound(s) described herein include a pharmaceutical composition comprising at least one compound as described herein and at least one pharmaceutically acceptable excipient. In certain embodiments, the composition is formulated for an administration route such as oral or parenteral, for example, transdermal, transmucosal (e.g., sublingual, lingual, (trans)buccal, (trans) urethral, vaginal (e.g., trans- and perivaginally), (intra)nasal and (trans)rectal, intravesical, intrapulmonary, intraduodenal, intragastrical, intrathecal, subcutaneous, intramuscular, intradermal, intra-arterial, intravenous, intrabronchial, inhalation, and topical administration. In certain embodiments, the compositions described herein are orally available compositions.

In some embodiments, compositions described herein may be in tablet or capsule dosage form. In some embodiments, compositions described herein are in tablet form. In some embodiments, compositions described herein are in capsule form.

In some embodiments, compositions described herein include amiselimod, and/or a pharmaceutically acceptable salt thereof, and a pharmaceutically acceptable excipient selected from the group consisting of mannitol, calcium hydrogen phosphate anhydrous, and talc.

In some embodiments, compositions described herein include amiselimod, and/or a pharmaceutically acceptable salt thereof, and one or more of mannitol, calcium hydrogen phosphate anhydrous, and talc.

In some embodiments, compositions described herein include amiselimod, and/or a pharmaceutically acceptable salt thereof, and pharmaceutically acceptable excipients comprising mannitol, calcium hydrogen phosphate anhydrous, and talc.

In some embodiments, compositions described herein are in capsule form and include amiselimod, and/or a pharmaceutically acceptable salt thereof, along with pharmaceutically acceptable excipients selected from the group consisting of mannitol, calcium hydrogen phosphate anhydrous, talc, and combinations thereof.

The compositions described herein may provide amiselimod at the doses set forth herein according to the described methods.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the compound(s) described herein are dictated by and directly dependent on (a) the unique characteristics of the therapeutic compound and the particular therapeutic effect to be achieved, and (b) the limitations inherent in the art of compounding/formulating such a therapeutic compound.

In certain embodiments, the compositions described herein are formulated using one or more pharmaceutically acceptable excipients or carriers. In certain embodiments, the compositions described herein comprise a therapeutically effective amount of a compound described herein and a pharmaceutically acceptable excipient.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions described herein are administered to the patient in dosages that range from one to five times per day or more. In other embodiments, the compositions described herein are administered to the patient in range of dosages that include, but are not limited to, once every day, every two, days, every three days to once a week, and once every two weeks. It is readily apparent to one skilled in the art that the frequency of administration of the various combination compositions described herein varies from individual to individual depending on many factors including, but not limited to, age, disease or disorder to be treated, gender, overall health, and other factors. Thus, administration of the compounds and compositions described herein should not be construed to be limited to any particular dosage regime and the precise dosage and composition to be administered to any patient is determined by the attending physician taking all other factors about the patient into account.

In certain embodiments, a composition as described herein is a packaged pharmaceutical composition comprising a container holding a therapeutically effective amount of a compound described herein, alone or in combination with a second pharmaceutical agent; and instructions for using the compound to treat, prevent, or reduce one or more symptoms of a disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions described herein include oral, nasal, rectal, intravaginal, parenteral, buccal, sublingual or topical. The compounds for use in the compositions described herein can be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions described herein are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compound(s) described herein can be in the form of tablets or capsules prepared by conventional means with pharmaceutically acceptable excipients such as binding agents (e.g., polyvinylpyrrolidone, hydroxypropylcellulose or hydroxypropyl methylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Compositions as described herein can be prepared, packaged, or sold in a formulation suitable for oral or buccal administration. A tablet that includes a compound as described herein can, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, dispersing agents, surface-active agents, disintegrating agents, binding agents, and lubricating agents.

Suitable dispersing agents include, but are not limited to, potato starch, sodium starch glycollate, poloxamer 407, or poloxamer 188. One or more dispersing agents can each be individually present in the composition in an amount of about 0.01% w/w to about 90% w/w relative to weight of the dosage form. One or more dispersing agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Surface-active agents (surfactants) include cationic, anionic, or non-ionic surfactants, or combinations thereof. Suitable surfactants include, but are not limited to, behentrimonium chloride, benzalkonium chloride, benzethonium chloride, benzododecinium bromide, carbethopendecinium bromide, cetalkonium chloride, cetrimonium bromide, cetrimonium chloride, cetylpyridine chloride, didecyldimethylammonium chloride, dimethyldioctadecylammonium bromide, dimethyldioctadecylammonium chloride, domiphen bromide, lauryl methyl gluceth-10 hydroxypropyl dimonium chloride, tetramethylammonium hydroxide, thonzonium bromide, stearalkonium chloride, octenidine dihydrochloride, olaflur, N-oleyl-1,3-propanediamine, 2-acrylamido-2-methylpropane sulfonic acid, alkylbenzene sulfonates, ammonium lauryl sulfate, ammonium perfluorononanoate, docusate, disodium cocoamphodiacetate, magnesium laureth sulfate, perfluorobutanesulfonic acid, perfluorononanoic acid, perfluorooctanesulfonic acid, perfluorooctanoic acid, potassium lauryl sulfate, sodium alkyl sulfate, sodium dodecyl sulfate, sodium laurate, sodium laureth sulfate, sodium lauroyl sarcosinate, sodium myreth sulfate, sodium nonanoyloxybenzenesulfonate, sodium pareth sulfate, sodium stearate, sodium sulfosuccinate esters, cetomacrogol 1000, cetostearyl alcohol, cetyl alcohol, cocamide diethanolamine, cocamide monoethanolamine, decyl glucoside, decyl polyglucose, glycerol monostearate, octylphenoxypolyethoxyethanol CA-630, isoceteth-20, lauryl glucoside, octylphenoxypolyethoxyethanol P-40, Nonoxynol-9, Nonoxynols, nonyl phenoxypolyethoxylethanol (NP-40), octaethylene glycol monododecyl ether, N-octyl beta-D-thioglucopyranoside, octyl glucoside, oleyl alcohol, PEG-10 sunflower glycerides, pentaethylene glycol monododecyl ether, polidocanol, poloxamer, poloxamer 407, polyethoxylated tallow amine, polyglycerol polyricinoleate, polysorbate, polysorbate 20, polysorbate 80, sorbitan, sorbitan monolaurate, sorbitan monostearate, sorbitan tristearate, stearyl alcohol, surfactin, Triton X-100, and Tween 80. One or more surfactants can each be individually present in the composition in an amount of about 0.01% w/w to about 90% w/w relative to weight of the dosage form. One or more surfactants can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable diluents include, but are not limited to, calcium carbonate, magnesium carbonate, magnesium oxide, sodium carbonate, lactose, microcrystalline cellulose, calcium phosphate, calcium hydrogen phosphate, and sodium phosphate, Cellactose® 80 (75% α-lactose monohydrate and 25% cellulose powder), mannitol, pre-gelatinized starch, starch, sucrose, sodium chloride, talc, anhydrous lactose, and granulated lactose. One or more diluents can each be individually present in the composition in an amount of about 0.01% w/w to about 90% w/w relative to weight of the dosage form. One or more diluents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable granulating and disintegrating agents include, but are not limited to, sucrose, copovidone, corn starch, microcrystalline cellulose, methyl cellulose, sodium starch glycollate, pregelatinized starch, povidone, sodium carboxy methyl cellulose, sodium alginate, citric acid, croscarmellose sodium, cellulose, carboxymethylcellulose calcium, colloidal silicone dioxide, crosspovidone and alginic acid. One or more granulating or disintegrating agents can each be individually present in the composition in an amount of about 0.01% w/w to about 90% w/w relative to weight of the dosage form. One or more granulating or disintegrating agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable binding agents include, but are not limited to, gelatin, acacia, pre-gelatinized maize starch, polyvinylpyrrolidone, anhydrous lactose, lactose monohydrate, hydroxypropyl methylcellulose, methylcellulose, povidone, polyacrylamides, sucrose, dextrose, maltose, gelatin, polyethylene glycol. One or more binding agents can each be individually present in the composition in an amount of about 0.01% w/w to about 90% w/w relative to weight of the dosage form. One or more binding agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable lubricating agents include, but are not limited to, magnesium stearate, calcium stearate, hydrogenated castor oil, glyceryl monostearate, glyceryl behenate, mineral oil, polyethylene glycol, poloxamer 407, poloxamer 188, sodium laureth sulfate, sodium benzoate, stearic acid, sodium stearyl fumarate, silica, and talc. One or more lubricating agents can each be individually present in the composition in an amount of about 0.01% w/w to about 90% w/w relative to weight of the dosage form. One or more lubricating agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Tablets can be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and U.S. Pat. No. 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Tablets can also be enterically coated such that the coating begins to dissolve at a certain pH, such as at about pH 5.0 to about pH 7.5, thereby releasing a compound as described herein. The coating can contain, for example, EUDRAGIT® L, S, FS, and/or E polymers with acidic or alkaline groups to allow release of a compound as described herein in a particular location, including in any desired section(s) of the intestine. The coating can also contain, for example, EUDRAGIT® RL and/or RS polymers with cationic or neutral groups to allow for time-controlled release of a compound as described herein by pH-independent swelling.

Methods of Treatment, Amelioration, and/or Prevention

In some embodiments, the disclosure includes methods of preventing, treating, and/or ameliorating ulcerative colitis (UC) as well as methods of reducing inflammation in the gastrointestinal (GI) tract in a subject in need thereof. Such methods include the administration of at least first and second doses of compositions described herein, wherein the first dose includes a greater amount of amiselimod as compared to the second dose. Due, in part, to amiselimod's lack of negative chronotropic activity (a known side effect of other S1P modulators), it has been surprisingly found that amiselimod may be used in the treatment methods described herein without requiring upward dose titration. Indeed, as demonstrated by the methods herein, amiselimod may be used to treat disease (e.g., UC) by providing loading amiselimod doses to achieve a selected in vivo concentration followed by respectively smaller maintenance amiselimod doses to maintain the selected in vivo concentration.

Etiology of UC

The exact cause of UC remains unknown. Barrier defects in colonic epithelial cells (colonocytes), mucous barrier and epithelial barrier are strongly implicated in the pathogenesis of UC. The damage that occurs in the colonic mucosa of UC patients is associated with an intense inflammatory cascade, including lymphocytic efflux. Several factors have been described as contributing to this pathophysiology, these include: reduced expression of proliferator-activated receptor gamma (PPAR-y, a negative regulator of NF-κB-dependent inflammation); alterations in trefoil factors (proteins that contribute to barrier integrity), dysbiosis, increased expression of Toll-like receptors 2 (TLR2) and TLR4, and upregulation of sphingosine-1-phosphate (S1P).

It is not clear whether some of these findings are causal or secondary to the primary inflammation in colon tissue.

Innate lymphoid cells (ILCs) might be central in the pathogenesis of UC through ILC3 (a major mediator of chronic intestinal inflammation). The possibility that ILCs might be drivers of disease pathogenesis has led to potential novel therapeutic targets. Another possible cause for the etiology of UC is an immune system dysfunction. Both innate and adaptive cellular immunity are keys to disease pathogenesis. UC is a modified T-helper-2 (Th2) disease. Colonic lamina propria cells from patients with UC were found to contain Th2-polarised T cells that produce interleukin-5 (IL-5) and IL-4 and IL-13 mRNA levels were significantly increased in rectal biopsies from patients with UC.

In addition, IL-13, produced by non-classical natural killer T cells (perhaps a member of the ILC family), is a key mediator of epithelial cytotoxicity and barrier dysfunction in ulcerative colitis. Recruitment of circulating leucocytes from the systemic circulation to the inflamed mucosa by release of chemo-attractants, such as CXCL8 (which is upregulated in patients with ulcerative colitis), is important for amplification of the inflammatory response. Proinflammatory cytokines upregulate the expression of adhesion molecules, e.g., mucosal addressing cellular adhesion molecule-1 (MadCAM-1), on the vascular endothelium of mucosal blood vessels, which promotes leucocyte adhesion and extravasation into the tissue, thus perpetuating the cycle of inflammation. MAdCAM-1, through interaction with $\alpha4\beta7$ integrin, mediates lymphocyte homing to gut-associated lymphoid tissue during inflammation.

Treatment of UC

The primary aim of the medical management of UC is to induce and maintain remission with the long-term goals of preventing disability, colectomy, and colorectal cancer. Targets for remission include resolution of clinical symptoms, defined as cessation of rectal bleeding and improvement in bowel habits, and endoscopic healing, which is frequently defined as an endoscopic Mayo Score of zero or one. First-line therapy in mild to moderate UC is the 5-ASA (5-aminosalicylic acid) drugs, which can be administered as suppositories, enemas, or oral formulations. Patients who do not respond or do not achieve remission on 5-ASA drugs can be treated with corticosteroids. However, corticosteroids should not be used for maintenance of remission because of a lack of long term efficacy and the risk of side effects. Patients with moderate UC can also be managed with biologic agents with or without immunomodulators (thiopurines or methotrexate) for induction of remission. Thiopurines (azathioprine or 6-mercaptopurine) can be used in patients with steroid-dependent moderate to severe disease to maintain remission. Anti-TNF-$\alpha$ drugs, such as infliximab, adalimumab, and golimumab, have been shown to be effective at inducing and maintaining remission in moderate to severe disease. A treatment of UC may be a treatment of mild to moderate UC, where mild UC is defined as a modified Mayo Score of 3 or 4 and moderate UC is defined as a modified Mayo Score of 5 to 8.

Therapeutics that target the multiple pathogenic pathways of UC are in development or have been recently approved, mostly for moderate to severe disease. These include $\alpha4$ integrin antagonists (e.g., vedolizumab, etrolizumab, AJM300), phosphodiesterase 4 (PDE4) inhibitors (e.g., apremilast), mitogen-activated protein kinase (MAPK) inhibitors (e.g. RDP-58 (delmitide acetate)), Janus kinase (JAK) inhibitors (e.g., tofacitinib, filgotinib, upadacitinib, TD-1473, and ASP015K), and sphingosine receptor modulators (e.g., ozamimod, etrasimod, and amiselimod).

Sphingosine-1-Phosphate (S1P) in UC

S1P is a structural, metabolic, and bioactive lipid involved in the regulation of various physiological responses, including cell growth, transformation, migration, and cell death. It is a multi-functional phospholipid mediator generated from sphingosine by sphingosine kinases and binds 5 types of G protein-coupled S1P receptors (S1P1, S1P2, S1P3, S1P4, and S1P5). S1P and S1P1 receptors play an essential role in lymphocyte egress from secondary lymphoid organs. In mice lacking lymphocytic S1P1 receptor, lymphocytes are unable to exit from secondary lymphoid organs to the periphery. Enhanced S1P concentrations, detected at the sites of inflammation in inflammatory diseases of the bowel, intensify inflammatory signaling, engagement of immune cells, and further release of other pro-inflammatory agents. The focus on S1P receptors in UC is defined by ubiquitous expression of these receptors in nearly all GI tissues and the possibility to amend inflammation-related pathologies via modification of S1P signaling mechanisms.

A method of preventing, treating, and/or ameliorating ulcerative colitis in a subject in need thereof includes the steps of: administering to the subject a first dose of amiselimod, or a pharmaceutically acceptable salt or enantiomer thereof, during a first administration period; and administering to the subject a second dose of amiselimod, or a pharmaceutically acceptable salt or enantiomer thereof, during a second administration period, wherein the first dose is larger than the second dose.

In various embodiments, the methods described herein exclude administration of amiselimod to any subject currently using or having used within the past 1-30 days any other sphingosine 1-phosphate (S1P) receptor modulators, non-oral (IV or rectal) corticosteroid, immunosuppressants, cyclosporine, mycophenolate mofetil, or thalidomide, tacrolimus, intravenous immunoglobulin, plasmapheresis, or cytapheresis therapy, any biologics or newly approved UC treatment agents (e.g., infliximab, adalimumab, certolizumab, golimumab, etanercept, vedolizumab, ustekinumab, tofacitinib, or natalizumab), Class I or Class III anti-arrhythmic drugs, calcium channel blockers, $\beta$-blockers, drugs identified as prolonging QT interval, and combinations of the foregoing.

In various embodiments, the methods described herein exclude administration of amiselimod to any subject using unstable doses of an agent selected from the group consisting of oral or rectal 5-ASAs and oral corticosteroids. As used herein, an "unstable dose" is a drug dose that has been changed within 28 days from a first dose of amiselimod according to the methods described herein.

In various embodiments, the treatment of inflammation in a subject's GI tract can be accomplished using any of the methods for treating UC described herein. In various embodiments, the inflammation in a subject's GI tract is a result of or caused by an inflammatory bowel disease (IBD) other than UC, UC, Crohn's disease (CD), celiac disease, irritable bowel syndrome (IBS), and the like. In some embodiments, the methods described herein may be provided for the treatment of mild to moderate UC. In some embodiments, the methods described herein may be provided for the treatment of mild UC. In some embodiments, the methods described herein may be provided for the treatment of moderate UC.

In various embodiments, administering the first dose to the subject does not induce a negative chronotropic effect in heart rate in the subject. Chronotropic effects in the heart can include changes in the heart rate or rhythm. Negative chronotropic effects are those that result in a decreased heart rate and include bradyarrhythmia (bradycardia).

At least in part due to the knowledge that S1P receptor modulators may induce negative chronotropic effects, skilled artisans have recognized that certain dosing regimens may be necessary to reduce or eliminate the incidence of chronotropic effects. For example, U.S. Pat. No. 8,492,441, specifically directs skilled artisans to administer S1P receptor modulators or agonists in such a way as to ensure that the initial dose (often called a loading dose) is lower than the standard daily dose, and the doses may be increased in one or more steps from the initial dose to the standard daily dose. Unlike S1P receptor modulator based therapies disclosed in the prior art, the unique safety and PK profile for amiselimod has led to the development of the methods described herein, which permit the delivery of an initial dose (i.e., loading dose) of amiselimod that is greater than a subsequent or ongoing maintenance dose of amiselimod in order to rapidly achieve a target steady state concentration.

The methods described herein include at least two doses where the initial dose (e.g., a first dose) is larger than the subsequent dose or doses (e.g., the second dose). For example, the initial dose may be administered during a loading dose phase of drug treatment, which may then be followed by subsequent, smaller doses during a maintenance dose phase of treatment. In some embodiments, the method includes administration of a first dose of a composition described herein and a second dose of a composition described herein.

The first dose is, in some embodiments, about 1.1 to about 5 times larger than the second dose, or about 1.5 to about 2.5 times larger than the second dose. In some embodiments, the first dose is about 1.1, 1.2, 1.3, 1.4, 1.5, 1.6, 1.7, 18, 1.9, 2.0, 2.1, 2.3, 2.4, 2.5, 2.6, 2.7, 2.8, 2.8, 2.9, 3.0, 3.2, 3.4, 3.6, 3.8, 4.0, 4.2, 4.4, 4.6, 4.8, or 5.0 times larger than the second dose. In some embodiments, the first dose is at least about 1.1, 1.2, 1.3, 1.4, 1.5, 1.6, 1.7, 18, 1.9, 2.0, 2.1, 2.3, 2.4, 2.5, 2.6, 2.7, 2.8, 2.8, 2.9, 3.0, 3.2, 3.4, 3.6, 3.8, 4.0, 4.2, 4.4, 4.6, 4.8, or 5.0 times larger than the second dose. In some embodiments, the first dose is at most about 1.1, 1.2, 1.3, 1.4, 1.5, 1.6, 1.7, 18, 1.9, 2.0, 2.1, 2.3, 2.4, 2.5, 2.6, 2.7, 2.8, 2.8, 2.9, 3.0, 3.2, 3.4, 3.6, 3.8, 4.0, 4.2, 4.4, 4.6, 4.8, or 5.0 times larger than the second dose. In various embodiments, the first dose is about 2 times larger than the second dose.

The first dose and the second dose are, in various embodiments, each daily doses. The first dose, when administered, is in some embodiments given to the subject once (QD), twice (BID), three (TID), or four (QID) times daily. In various embodiments, the first dose is administered to the subject once daily. The second dose, when administered, is in some embodiments given to the subject once (QD), twice (BID), three (TID), or four (QID) times daily. In various embodiments, the second dose is administered to the subject once daily.

Amiselimod has a half-life of about 400 hours. For example, amiselimod has a terminal half-life that is about 20 times longer than etrasimod, which has a half-life of about 17-20 hours. In a study, a daily dose of amiselimod achieved a therapeutic steady state after 14 days of 0.4 mg QD administration. On day 13, the steady-state AUC and Cmax for amiselimod 0.4 mg QD increased by 10-fold for amiselimod and by 4-fold for amiselimod-P compared with day 1. This increase in AUC and Cmax correlated with gradual decrease in absolute lymphocyte counts. The reduction in lymphocyte counts was maintained after amiselimod discontinuation, indicating a persistent therapeutic amiselimod AUC owing in part to the associated half-life. Accordingly, amiselimod may be administered in accordance with the methods described herein less frequently than once daily to achieve the desired treatment such, as for example, maintenance of Ulcerative Colitis. In some embodiments, the second dose may be administered during the second administration period (e.g., the maintenance dose phase) QD, BID, TID, or QID every other day during the second administration period or every two days during the second administration period or every three days during the second administration period or every four days during the second administration period or every five days during the second administration period or every six days during the second administration period or every seven days during the second administration period.

In some embodiments, the second dose may be administered during the second administration period (e.g., the maintenance dose phase) QD every other day during the second administration period or every two days during the second administration period or every three days during the second administration period or every four days during the second administration period or every five days during the second administration period or every six days during the second administration period or every seven days during the second administration period. In some embodiments, the second dose may be administered during the second administration period (e.g., the maintenance dose phase) BID every other day during the second administration period or every two days during the second administration period or every three days during the second administration period or every four days during the second administration period or every five days during the second administration period or every six days during the second administration period or every seven days during the second administration period. In some embodiments, the second dose may be administered during the second administration period (e.g., the maintenance dose phase) TID every other day during the second administration period or every two days during the second administration period or every three days during the second administration period or every four days during the second administration period or every five days during the second administration period or every six days during the second administration period or every seven days during the second administration period. In some embodiments, the second dose may be administered during the second administration period (e.g., the maintenance dose phase) QD, BID, TID, or QID every other day during the second administration period. In some embodiments, the second dose may be administered during the second administration period (e.g., the maintenance dose phase) QD every other day during the second administration period. In some embodiments, the second dose may be administered during the second administration period (e.g., the maintenance dose phase) BID every other day during the second administration period. In some embodiments, the second dose may be administered during the second administration period (e.g., the maintenance dose phase) TID every other day during the second administration period.

The first dose and the second dose can each include, independently, about 0.05 mg to about 10 mg of amiselimod. In some embodiments, the first and second dose each independently include about 0.05, 0.06, 0.07, 0.08, 0.09, 0.1, 0.2, 0.3, 0.4, 0.5, 0.6, 0.7, 0.8, 0.9, 1.0, 1.2, 1.4, 1.6, 1.8, 2, 3, 4, 5, 6, 7, 8, 9, or 10 mg of amiselimod. In some embodiments, the first and second dose each independently include at least about 0.05, 0.06, 0.07, 0.08, 0.09, 0.1, 0.2, 0.3, 0.4, 0.5, 0.6, 0.7, 0.8, 0.9, 1.0, 1.2, 1.4, 1.6, 1.8, 2, 3, 4, 5, 6, 7, 8, 9, or 10 mg of amiselimod. In some embodiments, the first and second dose each independently include at most about 0.05, 0.06, 0.07, 0.08, 0.09, 0.1, 0.2, 0.3, 0.4, 0.5, 0.6, 0.7, 0.8, 0.9, 1.0, 1.2, 1.4, 1.6, 1.8, 2, 3, 4, 5, 6, 7, 8, 9, or 10 mg of amiselimod.

In various embodiments, the first dose and second dose each independently include about 0.1 mg to about 1 mg of amiselimod, with the proviso that the first dose is larger than the second dose. In various embodiments, the first dose includes about 0.1, 0.2, 0.3, 0.4, 0.5, 0.6, 0.7, 0.8, 0.9, or 1.0 mg of amiselimod. In various embodiments, the first dose includes at least about 0.1, 0.2, 0.3, 0.4, 0.5, 0.6, 0.7, 0.8, 0.9, or 1.0 mg of amiselimod. In various embodiments, the first dose includes at most about 0.1, 0.2, 0.3, 0.4, 0.5, 0.6, 0.7, 0.8, 0.9, or 1.0 mg of amiselimod. In various embodiments, the first dose includes about 0.8 mg or about 0.4 mg.

Amiselimod doses can be formulated to contain any of the excipients described herein in the amounts described herein. In various embodiments, the amiselimod is formulated for oral administration. The oral dosage of amiselimod can include, in some embodiments, mannitol, calcium hydrogen phosphate anhydrous, and talc.

In some embodiments, the amiselimod dose delivered according to the methods described herein may be a composition in capsule form described in Table 1.

TABLE 1

Example Amiselimod Compositions

| Component | Function | Quantity (mg/capsule) 0.2 mg | 0.4 mg |
|---|---|---|---|
| amiselimod drug substance (HCl salt) (amiselimod free base form) | Active ingredient | 0.22 [1] (0.2) | 0.44 [1] (0.4) |
| Mannitol | Diluent | 28.39 | 28.28 |
| Calcium hydrogen phosphate anhydrous | Diluent | 28.39 [1] | 28.28 [1] |
| Talc | Lubricant | 3.00 | 3.00 |
| Total fill weight (mg) | — | 60.0 | 60.0 |
| Gelatin capsule Size #3[2] | Capsule shell | 1 piece | 1 piece |

[1] The actual weight of amiselimod drug substance is adjusted for potency. The amount of calcium hydrogen phosphate anhydrous is also adjusted according to the amount of amiselimod drug substance present.
[2] Gelatin capsule is composed of gelatin, titanium dioxide, sodium lauryl sulphate, and talc.

In some embodiments, the first administration period (e.g., the loading dose phase) is 1 to 21 days. In some embodiments, the first administration period is about 1, 2, 3, 4, 5, 6, 7, 8, 9, 10, 11, 12, 13, 14, 15, 16, 17, 18, 19, 20, or 21 days. In some embodiments, the first administration period at least about 1, 2, 3, 4, 5, 6, 7, 8, 9, 10, 11, 12, 13, 14, 15, 16, 17, 18, 19, 20, or 21 days. In some embodiments, the first administration period is at most about 1, 2, 3, 4, 5, 6, 7, 8, 9, 10, 11, 12, 13, 14, 15, 16, 17, 18, 19, 20, or 21 days. In various embodiments, the first administration period is 1 to 14 days. The first administration period is, in some embodiments, at least 11, 12, 13, or 14 days. The first administration period is, in some embodiments, at least 11 days.

The second administration period (e.g., the maintenance dose phase) is at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 days. In some embodiments, the second administration period is at most about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 days. In some embodiments, the second administration period is about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 days. In some embodiments, the second administration period is about 20 to 90 days. In some embodiments, the second administration period continues for as long as necessary to treat the subject. In various embodiments, the second administration period is about 1, 2, 3, 4, 5, 6, 7, 8, 9, 10, 11, or 12 months. In some embodiments, the second administration period is at least about 1, 2, 3, 4, 5, 6, 7, 8, 9, 10, 11, or 12 months. In some embodiments, the second administration period is at most about 1, 2, 3, 4, 5, 6, 7, 8, 9, 10, 11, or 12 months. In some embodiments, the second administration period is about 1, 2, 3, 4, 5, 6, 7, 8, 9, 10, 11, or 12 years. In some embodiments, the second administration period is at least about 1, 2, 3, 4, 5, 6, 7, 8, 9, 10, 11, or 12 years. In some embodiments, the second administration period is at most about 1, 2, 3, 4, 5, 6, 7, 8, 9, 10, 11, or 12 years. In some embodiments, the second administration period continues for the lifetime of the subject.

The first or second dose of amiselimod can be any of the compositions described herein, including those of various dosage forms. The amount of the amiselimod dose notwithstanding, the first or second dose of amiselimod can be compositionally identical or different (e.g. different types or amounts of pharmaceutically acceptable excipients or carriers), and each can include at least one pharmaceutical excipient or carrier as described herein. Amiselimod, in some embodiments, is the only active agent in the first or second dose. In some embodiments, the method of administering amiselimod further includes administering at least one additional therapeutic agent. The additional therapeutic agent can be administered either sequentially or concurrently with amiselimod. Unit dose forms of amiselimod can include amiselimod and at least one additional therapeutic agent. In various embodiments, the additional therapeutic agent is an anti-inflammatory agent.

Suitable additional therapeutic agents include, without limitation, 5-ASAs such as mesalamine, sulfasalazine, olsalazine, or balsalazide and the like; NSAIDs such as aspirin, ibuprofen, naproxen, diclofenac, celecoxib, mefenamic acid, etoricoxib, or indomethacin, and the like; steroids such as prednisone, beclomethasone, or budesonide.

In certain embodiments, administering the compositions described herein to the subject allows for administering a lower dose of the additional therapeutic agent as compared to the dose of the additional therapeutic agent alone that is required to achieve similar results in treating UC or inflammation in the GI tract in the subject. For example, in certain embodiments, the compositions described herein enhance(s) the activity of the additional therapeutic agent, thereby allowing for a lower dose of the additional therapeutic agent to provide the same effect in the subject.

In certain embodiments, the composition(s) described herein and the additional therapeutic agent are co-administered to the subject. In some embodiments, the composition(s) described herein and the additional therapeutic agent are administered to the subject sequentially. In some embodiments, the composition(s) described herein and the additional therapeutic agent are administered to the subject simultaneously. In some embodiments, the first dose of a composition described herein is co-administered with the additional therapeutic agent. In some embodiments, the second dose of a composition described herein is co-administered with the additional therapeutic agent. In some embodiments, the first dose of a composition described herein and the second doses of a composition described herein are co-administered with the additional therapeutic agent.

EXAMPLES

Various embodiments described herein can be better understood by reference to the following Examples which are offered by way of illustration. The scope of the methods described herein is not limited to the Examples given herein.

Example 1

The safety of amiselimod in healthy subjects was evaluated in a Phase 1 randomized, double-blind, placebo-controlled study where the dose of amiselimod was upwardly titrated.

The objective of this study was to evaluate the safety profile of amiselimod, a selective sphingosine 1-phosphate receptor modulator which has been shown to regulate lymphocyte trafficking and is in development for the treatment of inflammatory bowel disease.

A randomized, double-blind, multiple-dose, placebo-controlled, parallel study with a nested crossover design evaluated the safety and tolerability profile of amiselimod. Healthy adults were randomized in a 2:1:1 ratio during a 28-day treatment period accordingly: a single dose of placebo followed by oral amiselimod (upwardly titrated in doses ranging from 0.4 to 1.6 mg to achieve steady-state concentrations); a single dose of oral moxifloxacin 400 mg followed by placebo; or placebo followed by a single dose of moxifloxacin 400 mg (for the safety analysis, moxifloxacin arms were combined). The safety population included all subjects who received at least one dose of treatment. Adverse events (AE) and serious AEs were collected. Treatment-emergent AEs were defined as an AE that was starting or worsening at the time of or after study drug administration. Changes in clinical laboratory parameters (including lymphocyte counts), physical examinations, vital signs, and electrocardiogram parameters (including heart rate, PR, QRS, and QT intervals) were recorded. Subjects were permitted to withdraw if lymphocyte counts were $\leq 0.2\times10^9$/L.

The safety population included 190 subjects of which 95 received amiselimod and 95 were in the combined moxifloxacin group. Subjects were 40% female, 83% white, and the mean (standard deviation) age was 39.0 (8.8) years. The discontinuation rate was 8% (n=8) in the amiselimod group and 4% (n=4) in the moxifloxacin group. Three subjects discontinued because they met the stopping criteria for low lymphocyte counts. One subject experienced an amiselimod-related serious AE of atrial fibrillation on day 26 (after receiving amiselimod 1.6 mg for 3 of the preceding 4 days) that required hospitalization, cardioversion, and led to discontinuation. No deaths were reported. All other AEs were mild to moderate in severity. Decreased white blood counts were the most commonly reported TEAE (Treatment-Emergent Adverse Events), followed by headache and constipation (Table 2).

TABLE 2

Treatment-Emergent Adverse Events (>5%) by Treatment Group-Number of Subjects Reporting an Event (% of Subjects Dosed)

| Adverse Event, n (%) | Amiselimod (Days 1-13) n = 95 | Amiselimod (Days 14+) n = 92 | Moxifloxacin (Days 1-26) n = 95 | Moxifloxacin (Days 27+) n = 46 |
|---|---|---|---|---|
| Number of subjects with an adverse event | 55 (58) | 57 (62) | 49 (52) | 7 (15) |
| White blood cell count decreased | 18 (19) | 13 (14) | 0 | 0 |
| Constipation | 8 (8) | 6 (7) | 11 (12) | 0 |
| Dizziness | 5 (5) | 6 (7) | 1 (1) | 1 (2) |
| Headache | 4 (4) | 11 (12) | 12 (13) | 0 |
| Upper respiratory tract infection | 1 (1) | 6 (7) | 1 (1) | 0 |

Reductions in white blood counts returned to normal range after study discontinuation without sequelae. Decreased neutrophils, lymphocytes and hemoglobin, and increased creatine kinase, alanine aminotransferase, and aspartate aminotransferase were reported, all of which resolved without sequelae. The mean absolute lymphocyte count for amiselimod exhibited a gradual decrease from predose (1.681 thou/μL) to a nadir of 0.424 thou/μL on day 27 (FIG. 1). Changes to vital signs, physical examinations, and ECG parameters were within normal limits.

This study demonstrates that multiple, upwardly titrated doses of amiselimod are generally well tolerated in healthy subjects.

Example 2

A randomized, double-blinded, placebo controlled, 3-arm, multi-center, parallel-group study with an open-label extension period will be conducted with amiselimod. The primary objective of this study will be to assess the efficacy and safety of oral amiselimod (MT-1303) compared to placebo at 12 weeks in subjects with active mild to moderate ulcerative colitis.

The secondary objective will be to assess the efficacy and safety of maintenance treatment with open-label amiselimod for up to 36 weeks following completion of the Double-Blind Period.

Study Design

The study includes a Screening Period (of up to 28 days) and a 12-week Double-Blind Treatment Period (Day 1 through Day 85) for all subjects. Subjects completing the study through Day 85 will be given the opportunity to continue in the OLE Period of the study, if eligible, to receive treatment through Week 48 (Day 337) with a safety follow-up at Week 60 (Day 421). Subjects who choose to not participate in the OLE Period or who are not eligible will be followed for 84 days following the Double-Blind Period in a Safety Follow-up Period through Week 24 (Day 169/EOS).

Approximately 336 subjects will be randomly assigned in a 1:1:1 ratio (approximately 112 per treatment group) to receive 1 of 3 treatments for 12 weeks during the Double-Blind Period. The following dose groups will be evaluated.

Group A (low dose): Amiselimod loading dose of 0.4 mg QD (Day 1-14) then maintenance dose of 0.2 mg QD (Day 15-85);

Group B (high dose): Amiselimod loading dose of 0.8 mg QD (Day 1-14) then maintenance dose of 0.4 mg QD (Day 15-85);

Group C (placebo): Matching placebo, QD.

Approximately 20 subjects per treatment group will participate in serial PK sampling at selected sites. The remaining subjects will have sparse PK samples collected. The randomization will be stratified by severity (mild UC [modified Mayo Score of 3 or 4] or moderate UC [modified Mayo Score of 5 to 8]) and concurrent corticosteroid use (Y/N). A maximum of 80% of subjects randomized will have moderate UC and a maximum of 30% of subjects randomized will have mild UC. Assessments performed during the Day 85 Visit will serve as baseline assessments for subjects enrolling in the OLE (Open-label extension) Period.

Figure 2:
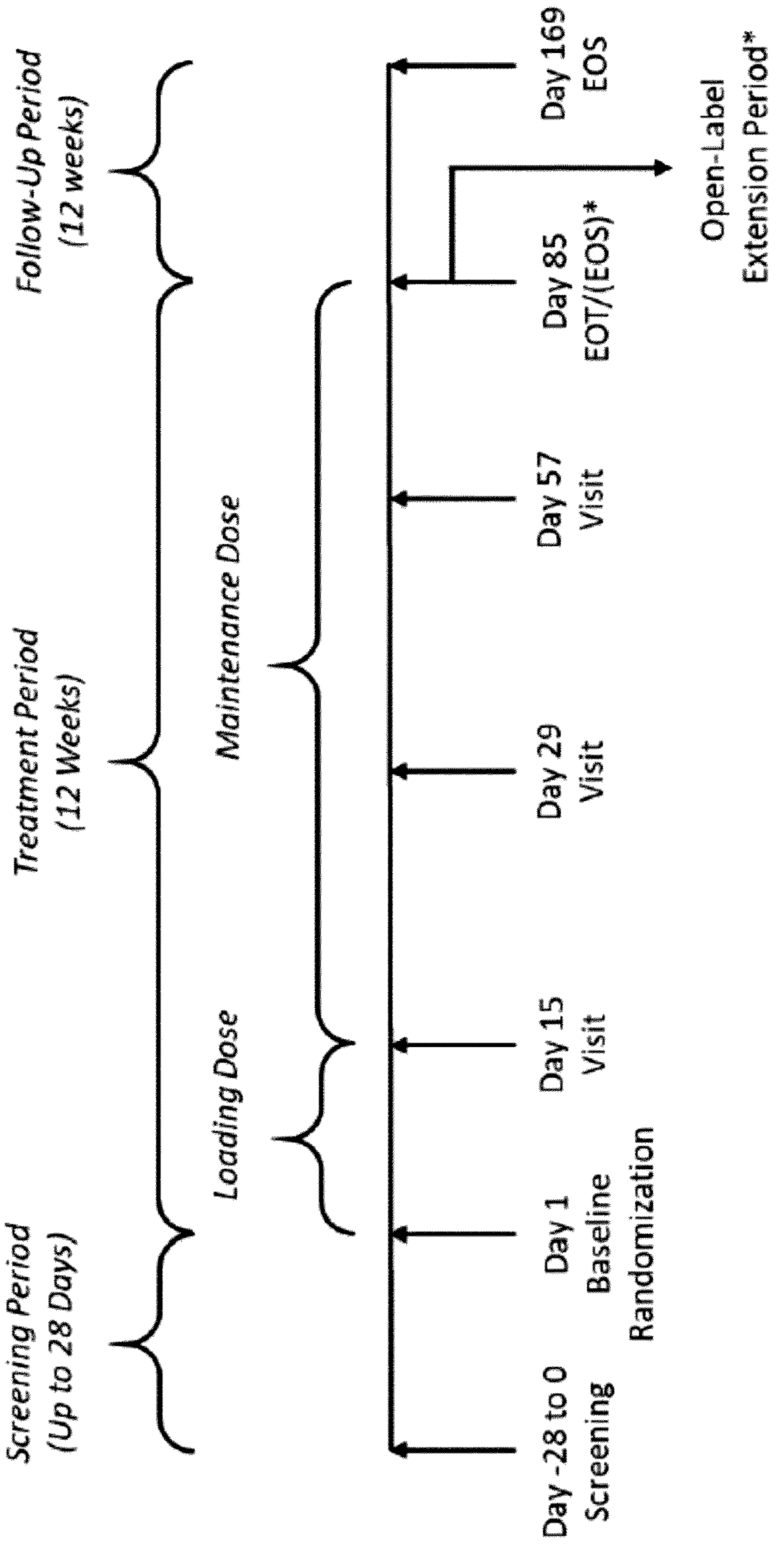
FIG. 2 shows a timeline of the double-blind period for a proposed amiselimod study.
Figure 3:
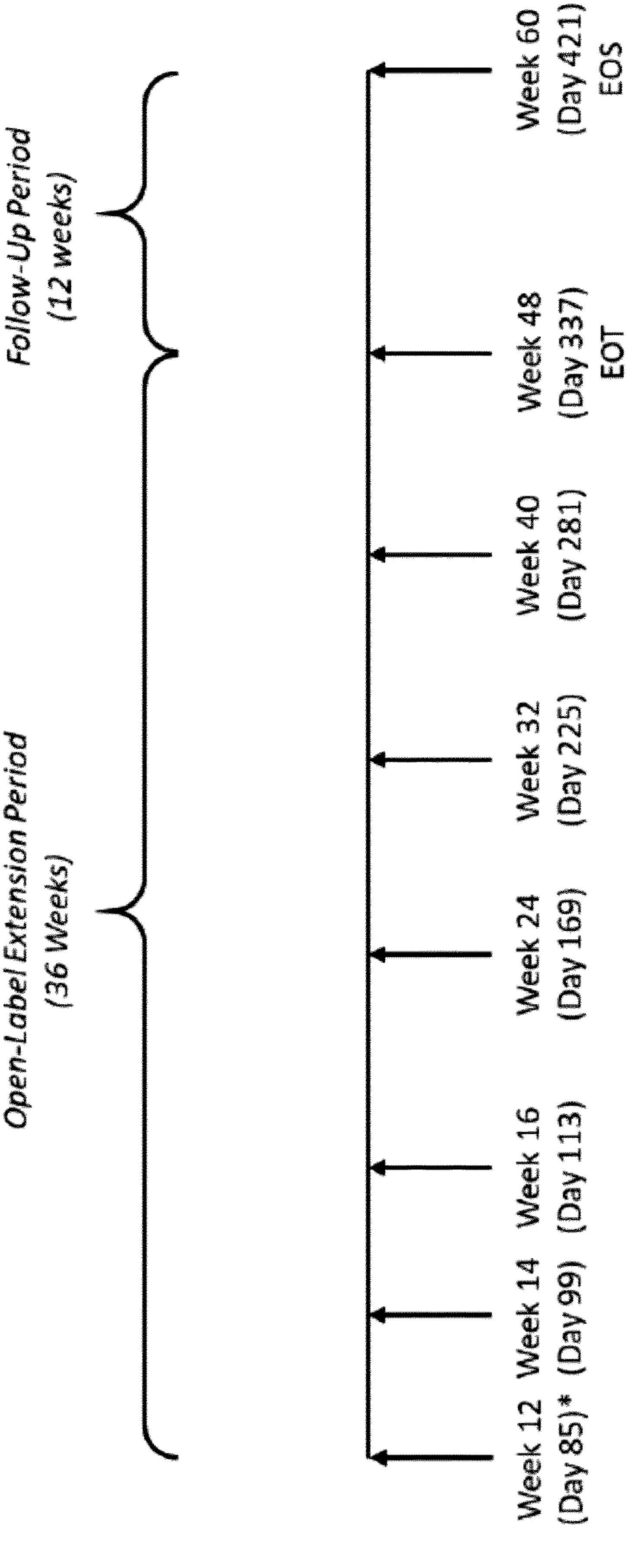
FIG. 3 shows a timeline of the open-label extension (OLE) period for a proposed amiselimod study.

For subjects not proceeding into the OLE Period, the final dose on Day 85 will be according to the randomization assignment for the Double-Blind Period (i.e., blinded placebo or active IMP). For subjects enrolling in the OLE Period, the Day 85 dose will be the first dose of open-label amiselimod for the OLE Period (i.e., 0.4 mg QD). A diagram of the study design for the Double-Blind Period is provided in FIG. 2. A diagram for the OLE Period is provided in FIG. 3.

Selection of Study Population

Approximately 336 subjects (112 per treatment group) at approximately 175 clinical sites in North America, Europe, Africa, and the Asia Pacific Region will be enrolled in the study.

Eligibility Inclusion Criteria

For Investigator questions regarding subject eligibility or clinical significance of abnormalities, discussion with the study Medical Monitor is strongly encouraged. To be eligible to participate in this study, candidates must meet the following eligibility criteria during the Screening and Baseline Visits or at the timepoint specified in the individual eligibility criterion listed:

1. Male or female subjects aged between 18 to 75 years (inclusive) at the time of the subject's signing of the informed consent.
2 Normal vital signs. • afebrile, • heart rate 55-100 bpm, • systolic blood pressure >90 and <150 mmHg, • diastolic blood pressure >50 and <90 mmHg, • respiration rate >10 and <20/min.
3 Diagnosis of active mild to moderate UC (modified Mayo Score of 3 to 8) confirmed at least 12 weeks prior to randomization by clinical and endoscopic evidence (corroborated by a histopathology report).
   Mild UC is defined as a modified Mayo Score of 3 or 4.
   Moderate UC is defined as a modified Mayo Score of 5 to 8.
4. An endoscopic subscore from screening colonoscopy of >2 as determined by a central reviewer.
5. Evidence of active UC extending ≥15 cm from the anal verge confirmed by a screening colonoscopy.
6. If subjects are receiving oral or rectal 5-aminosalicylates (5-ASAs) or oral corticosteroids (≤20 mg prednisolone equivalent) for treatment of their UC, they must be on a stable dose for at least 28 days prior to randomization.
7. All women of childbearing potential (WOCBP) must have a negative serum pregnancy test at the Screening Visit and a urine pregnancy test at each subsequent study visit and agree to use an acceptable method of contraception throughout their participation in the study and for 12 weeks after the last dose of IMP.
8. Willingness and ability to complete training in the use of the subject diary and to complete the subject diary in a timely manner throughout the study.

Exclusion Criteria

Candidates will be excluded from study entry if any of the following exclusion criteria exist at Screening or Baseline Visits or at the timepoint specified in the individual criterion listed.

Exclusion Criteria Related to Ulcerative Colitis

1. Diagnosis of Crohn's disease, indeterminate colitis, colitis (pseudomembranous, microscopic, or ischemic) or coeliac disease.
2. Current or recent (within 12 weeks prior to randomization) evidence of fulminant colitis, abdominal abscess, toxic megacolon, bowel obstruction, or bowel perforation.
3. Diagnosis of proctitis, defined as a rectal inflammation within 15 cm from the anal verge.
4 History or evidence of any colonic resection or subtotal colectomy within 1 year prior to randomization.
5. History or evidence of ileostomy, colostomy, or known fixed symptomatic stenosis of the intestine.
6. History or evidence of unresected adenomatous colonic polyps or colonic mucosal dysplasia.
7. Current need for, or anticipated need for surgical intervention for UC during the study.

Exclusion Criteria Related to General Health and Concomitant Conditions

8. Clinically significant infections (e.g., pneumonia, pyelonephritis, septicemia) within 4 weeks prior to randomization or previous clinically significant infections requiring hospitalization within 6 months prior to randomization
9. Active SARS-COV-2 infection or complications related to COVID-19.
10. History of lymphoma or other lymphoproliferative disease.
11. Active or latent tuberculosis, as evidenced by any of the following,
    a. History of tuberculosis.
    b. A positive or indeterminate result for QuantiFERON-TB Gold® (or T-SPOT®) during the screening period. If an indeterminate result for QuantiFERON-TB Gold (or T-SPOT) is confirmed, a re-test can be allowed once only.
    c. A positive or indeterminate result for chest X-ray that cannot exclude active or latent tuberculosis during the Screening Period.
12. Infections of hepatitis B, hepatitis C, human immunodeficiency virus (HIV), or varicella zoster virus (VZV) as evidenced by any of the following,
    a. History of hepatitis B, hepatitis C.
    b. Positive results for HBV, HCV, or HIV tests during the screening period.
    c. History of shingles outbreak.
13. History of or currently active primary or secondary immunodeficiency.
14. History of progressive multifocal leukoencephalopathy (PML) or presence of PML as determined by a positive PML objective checklist prior to randomization.

15. History or presence of demyelinating diseases.
16. *C. difficile* colitis/diarrhea within 60 days of the Screening Visit. Rescreening may occur 7 days after successful treatment for *C. difficile*.
17. Receipt of a live or live-attenuated vaccine (including VZV (varicella zoster virus) vaccine) within 4 weeks prior to randomization. (Note: non-live vaccinations are permitted.)
18. Recent (within the last 6 months) occurrence of myocardial infarction, unstable angina, stroke, transient ischemic attack, decompensated heart failure with hospitalization, or Class III/IV heart failure.
19. History of Mobitz Type II 2nd degree or 3rd degree atrioventricular (AV) block or sick sinus syndrome.
20. Ongoing treatment with Class I or Class III anti-arrhythmic drugs, or with heartrate-lowering calcium-channel blockers (e.g., verapamil or diltiazem), β-blockers, or with any other drugs which can reduce the heart rate (e.g., ivabradine, magnesium sulfate).
21. Known high risk for QT/QTc prolongation (e.g., family history of long QT syndrome or sudden death).
22. History or presence (within 5 years prior to screening) of malignancy, except for successfully treated basal cell and in situ squamous cell carcinomas of the skin.
23. History or presence of macular oedema (as assessed by OCT (optical coherence tomography) during screening), uveitis, or evolutive retinopathy, or any other condition that could increase the risk of macular oedema in the opinion of the Investigator.
24. Diabetes mellitus type 1 OR diabetes mellitus 2 with use of insulin or with >8 years disease duration after its diagnosis or with significant comorbid conditions (e.g., retinopathy, nephropathy, or neuropathy). Subjects with hemoglobin A1c (HbA1c)>7.5% during the screening period will also be excluded.
25. History or evidence of substance abuse (e.g., drug or alcohol), or any other factor (e.g., serious psychiatric condition) that limits the subject's ability to cooperate with the study procedures.

Exclusion Criteria Related to Administered Medications

26. History or evidence of two or more failures with biologic treatment for UC (primary non-responders).
27. Unstable dose of oral or rectal 5-ASAs or oral corticosteroids within 28 days prior to the Screening Visit.
28. Use of any of the following within 28 days prior to the Screening Visit or as designated:
    a. Non-oral (IV or rectal) corticosteroid.
    b. Cyclosporine, mycophenolate mofetil, or thalidomide.
    c. Tacrolimus.
    d. Intravenous immunoglobulin, plasmapheresis, or cytapheresis therapy.
    e. Any biologics or newly approved UC treatment agents (e.g., infliximab, adalimumab, certolizumab, golimumab, etanercept, vedolizumab, ustekinumab, tofacitinib, or natalizumab) within 8 weeks of the Screening Visit.
29. Use of immunosuppressants (e.g., AZA, 6-mercaptopurine, or methotrexate) 28 days prior to randomization.
30. Unstable dose of probiotics within 14 days prior to the Screening Visit.
31. Unstable dose of antidiarrheals (loperamide, diphenoxylate) within 14 days prior to the Screening Visit. 3
32. Use of enemas or suppositories (other than stable dose of 5-ASAs) for treatment of UC within 14 days prior to the Screening Visit.
33. Use of fecal microbiota transplantation (FMT) within 12 months prior to the Screening Visit.
34. History or evidence of use of lymphocyte-depleting therapies (e.g., anti-CD4, cladribine, rituximab, ocrelizumab, cyclophosphamide, mitoxantrone, total body irradiation, bone marrow transplantation, alemtuzumab, daclizumab).
35. For WOCBP, initiation of oral contraceptives, or having an unstable dose of oral contraceptives, within 12 weeks prior to the Screening Visit.
36. History of non-response or treatment failure with sphingosine 1-phosphate (S1P) receptor modulators including amiselimod, fingolimod, ozanimod, and etrasimod.
37. Known history of allergy, hypersensitivity or any serious reaction to any component of the IMP (e.g., mannitol or gelatin).
38. Previous treatment with any investigational agent within 12 weeks prior to randomization OR 5 half-lives of the investigational product, whichever is longer.
39. Plan to participate or are currently participating in any other interventional clinical trial (in which an investigational treatment or approved therapy for investigational use is administered) during this study.

Exclusion Criteria Related to ECG and PFT Findings

40. Low heart rate (<55 beats per minute [bpm]), in 12-lead ECG at screening or randomization (pre-dose).
41. Corrected QT interval using Fridericia's formula (QTcF)≥470 milliseconds (msecs) for females and ≥450 msec for males in 12-lead ECG at screening or randomization (pre-dose).
42. Any conduction abnormalities, e.g., Wolff Parkinson White.
43. Clinically significant abnormal findings in 12-lead ECG (at screening or randomization [pre-dose]) and/or in 24-hour ECG (at screening) that the Investigator considers may jeopardize the subject's health (e.g., acute ischemia, conduction abnormalities, or arrhythmias).
44. Forced expiratory volume in one second (FEV1) or forced expiratory vital capacity (FVC)<70% of predicted values at screening.
45. For sites where DLCO will be assessed, the value (mL/min/mmHg) is <80% of the predicted normal value for age, height, and gender.

Exclusion Criteria Related to Laboratory Findings

46. Any of the following laboratory abnormalities during the screening period:
    a. Hemoglobin (Hb)<9.0 g/dL.
    b. White blood cell (WBC) count $<3.50\times10^9$/L (<3,500/μL).
    c. Neutrophil count $<1.50\times10^9$/L (<1,500/μL).
    d. Lymphocyte count $<0.80\times10^9$/L (<800/μL).
    e. Aspartate aminotransferase (AST) or alanine aminotransferase (ALT)>2× the upper limit of normal (ULN).
    f. Bilirubin >1.5× the ULN. Subjects with Gilbert's syndrome may be enrolled with total bilirubin up to 5.0 mg/dl.
47. Positive stool tests for enteric pathogens, pathogenic ova or parasites, or *Clostridium difficile* (*C. difficile*) within 60 days prior to the Screening Visit.
48. (For female subjects only) A positive pregnancy test at Screening Visit (serum betahuman chorionic gonadotropin [hCG] level or urine dipstick) or Baseline Visit (urine dipstick) except for provided proof of menopause (hormonal or surgical). Subjects who are breast-feeding are also excluded.

General Exclusion

49. Any physical or mental conditions which would interfere with the study participation, collection of data, or study completion.
50. Other unspecified reasons that, in the opinion of the Investigator or Sponsor, make the subject unsuitable for enrollment.

Subject Completion

The subject has completed the study at the time of the last scheduled study procedures. This will be Day 169 (Week 24) for subjects that do not continue into the OLE Period and Day 421 (Week 60) for subjects that complete the OLE Period.

Subject Discontinuation

All subjects are free to withdraw from participating in this study at any time for any reason, specified or unspecified, and without prejudice. No constraints will be placed on ordinary subject management, and subjects, when appropriate, will be placed on other conventional therapy upon request or whenever clinically necessary as determined by their physician. Withdrawal of the subject from treatment with IMP or from the study will be considered, through consultation between the Investigator and the Sponsor, or designee, for any of the following reasons:

- The subject withdraws consent.
- It is necessary for the subject to take a prohibited medication or the subject takes a prohibited medication.
- A confirmed absolute lymphocyte count (ALC)$\leq 0.2\times10^9$/L.
  - If a single ALC value of $\leq 0.2\times10^9$/L was reported, a second value will be obtained within 48 hours. The subject will remain on IMP during this time unless otherwise indicated.
  - If the repeat value was $>0.2\times10^9$/L, the subject will continue treatment without interruption.
  - If the repeat value was $\leq 0.2\times10^9$/L, treatment with IMP will be discontinued and lymphocyte counts will be closely monitored. In addition, subjects should complete the End of Treatment (EOT) Visit. Subjects with an ALC of $\leq 0.2\times10^9$/L should be monitored on a weekly basis until their ALC value reaches the lower limit of normal (LLN).
- Development of any clinically significant abnormalities detected in the 12-lead safety ECGs, including but not limited to:
  - New onset second-degree AV block, Mobitz Type II.
  - New onset third-degree AV block.
  - Confirmed QTc>500 msec and/or QTc increase from Baseline of >60 msec measured on 2 occasions at least 1 hour apart.

Baseline safety ECGs will be defined as pre-dose Day 1. Subjects with any clinically significant abnormal ECG should be excluded and referred to a cardiologist for necessary management and follow-up.

- The subject's nonsleeping HR drops below 45 bpm based on safety ECG monitoring and the Investigator considers it clinically significant.
- The subject has an increase in ALT and/or AST of >3×ULN with a concurrent increase in total bilirubin of >2×ULN or with the appearance of relevant clinical symptoms and no evidence of alternative etiology (e.g., Gilbert's syndrome).
- The subject has an increase in ALT and/or AST >5×ULN.—If a single ALT and/or AST value >5×ULN was reported, a second value will be obtained within 48 hours. The subject will remain on IMP during this time unless otherwise indicated.—If the repeat value was ≤5×ULN, the subject will continue treatment without interruption.—If the repeat value was >5×ULN, treatment with IMP will be discontinued.
- The subject develops an increase in ALT and/or AST >8×ULN: a second value will be obtained as soon as possible (within 24 hours); IMP should be withheld until confirmation of the abnormal value is received. If confirmed, IMP should be permanently discontinued.
- Any subject with elevated ALT/AST meeting the above criteria should be monitored until ALT/AST reaches Baseline levels.
- The subject develops macular oedema during the study.
- The subject experiences an intolerable AE or SAE.
- The subject enrolls into another interventional clinical study in which an investigational treatment or approved therapy for investigational use is administered.
- The subject becomes pregnant. Study treatment must be discontinued immediately.

Report the pregnancy according to the instructions in Section 7.5.2.

- The subject is unwilling or unable to comply with the protocol.
- At the discretion of the Investigator or Sponsor.
- Investigator decision that it is not in the best medical interest of the subject to continue participation in the investigation Prior to discontinuing a subject, every effort should be made to contact the subject, schedule a final study visit to obtain as much follow-up data as possible and to retrieve all study materials. Subjects withdrawn or discontinued prior to Day 85 will undergo the end of treatment procedures per the scheduled assessments for the Day 85/EOT Visit. Subjects withdrawn or discontinued during the OLE Period will undergo the end of treatment procedures per the scheduled assessments the Week 48 (Day 337/EOT) Visit. For both the Double-Blind and OLE Periods, all subjects will be encouraged to return 84 days (+10 days) after study drug discontinuation for the Safety Follow-up Visit. Subject withdrawals will be documented clearly on the source documents and applicable case report forms (eCRFs). Notification of subject withdrawals will be made to the Sponsor, or designee. A subject that withdraws from the study or is lost to follow-up will not be replaced.

Lost to Follow-up

Subjects who do not return for scheduled visits, as defined by the visit schedule may be considered lost to follow-up. The site will attempt to contact the subject through a minimum of 2 telephone calls. If the subject still cannot be contacted the site will send a certified letter, or similar verified delivery, to the last known address of the subject. If no contact is made by the subject, the site will consider the subject lost to follow-up. All follow-up attempts will be documented and kept with the subject's source documentation, and the applicable eCRFs will be completed.

Study Duration

The planned enrollment period is approximately 24 months. Each subject will be screened for up to 4 weeks followed by a 12-week Double-Blind Period. Subjects enrolling in the OLE Period of the study will have up to an additional 36 weeks of study treatment (through Week 48) with a safety follow-up 12 weeks after completion of treatment (Week 60). Subjects not enrolling in the OLE period of the study, will be followed for 12 weeks following completion of treatment (Week 24). The total expected study duration for the both the Double-Blind and the OLE Period is approximately 40 months.

Treatments

Amiselimod for this study will be provided as either a 0.2 mg or 0.4 mg capsule. For the Double-Blind Period, subjects will be randomized into one of 3 groups: Group A, Group B, or Group C. The 0.2 mg, 0.4 mg, and placebo capsules will look identical to maintain the blind. The Investigator, site staff, subject and Sponsor study personnel (or their designees) will be blinded to the study group to which the subject is randomized. Subjects should take the IMP at approximately the same time each day. Subjects will be dosed as follows.

Loading dosage (Day 1-14):

- Group A (low dose): two 0.2 mg amiselimod capsules, orally, QD,
- Group B (high dose): two 0.4 mg amiselimod capsules, orally, QD,
- Group C (placebo): two placebo capsules, orally QD.

After the first 14 days of dosing, all subjects will be switched from two capsules daily to one capsule daily and dosed as follows:

Maintenance dosage (Day 15-85):

- Group A (low dose): one 0.2 mg amiselimod capsule, orally, QD,
- Group B (high dose): one 0.4 mg amiselimod capsule, orally, QD,
- Group C (placebo): one placebo capsule, orally QD.

Subjects who continue into the OLE Period of the study will receive open-label amiselimod at 0.4 mg QD through Week 48 (Day 337).

Efficacy and Safety Variables

Primary Efficacy Variables

The modified Mayo Score will be used for the primary efficacy evaluation. The Mayo Score for ulcerative colitis disease activity provides an assessment of disease severity and can be used to monitor subjects during therapy. Scoring is accomplished by summation of subscores for endoscopic findings, stool frequency, rectal bleeding, and/or the Physician Global Assessment (PGA) with higher scores indicating worse severity. Each subscore ranges from 0 to 3. The primary efficacy analysis for this study will use the modified Mayo Score defined as the sum of the endoscopy findings subscore+stool frequency subscore+rectal bleeding subscore, with a range from 0 to 9. Endoscopy will be conducted to determine Mayo endoscopic subscore. Both local and central reading of the results will occur. The endoscopic subscore for endpoint analysis will be based on the centrally read endoscopic results. The rectal bleeding subscore and stool frequency subscore are evaluated based on patient-reported symptoms. Subjects will complete a daily diary to record their worst daily rectal bleeding and stool frequency.

Secondary and Exploratory Efficacy Variables

In addition to the modified Mayo Score for the primary efficacy analysis, various iterations of Mayo scoring using endoscopic findings, stool frequency, rectal bleeding and/or the Physician Global Assessment (PGA) will be assessed for secondary and exploratory analyses. These include the complete Mayo Score (endoscopic+stool frequency+rectal bleeding+PGA subscores), the 2-component Mayo Score (rectal bleeding+endoscopic subscores) and clinical and remission outcomes based on Mayo scoring. The original Geboes index core (OGS) from the endoscopy will be provided to the Sponsor by the central reviewer. UC-related biomarkers will be examined. Blood samples obtained for safety laboratory evaluations will also be used to determine serum CRP levels. Stool samples will be collected to determine the presence/absence of fecal calprotectin and fecal lactoferrin. Subject assessment of improvement and quality of life will be assessed with the PGI-C and the EQ-5D-3L, respectively.

Safety Variables

Adverse Events (AEs) and Serious Adverse Events (SAEs)

AEs and SAEs will be collected throughout the study and graded for severity and relationship to IMP.

Physical Examination

A full physical examination will be performed at the Screening Visit and repeated at the Baseline Visit. Symptom-driven physical examinations will be performed at other visits.

Vital Signs

Body temperature, respiratory rate, blood pressure, and HR will be measured.

Blood pressure and HR measurements will be performed with subjects in a supine position for at least 5 minutes, except when they are seated or semi-reclined because of study procedures and/or AEs (e.g. nausea, dizziness) or if deemed necessary by the Investigator or designee.

Vital signs will be measured on Day 1 prior to the first dose. At all other visits, vital signs will be measured prior to dosing. When scheduled at the same time as a blood draw, vital signs will be performed prior to the blood collection.

ECG Monitoring

A subject will be withdrawn from the study by the Investigator or designee if, in their medical judgment, ECG findings are present which make continued study participation not in the subject's best interest or the subject meets discontinuation qualifications as described herein.

24-Hour ECGs

Twenty-four (24) hour monitors will be used to collect continuous ECG data at the Screening Visit to exclude subjects with heart conditions. Data collected from the 24-hours after the Screening Visit will be reviewed by a central reviewer prior to or at the Baseline Visit for determination of eligibility.

Collection of 24-hour ECGs will start within 1 hour prior to IMP dose.

Standard 12-Lead ECGs

On-study ECGs are planned as standard, single 12-lead ECGs interpreted on-site by the Investigator or designee. Consultation with the central ECG reviewer may be done if needed. Subjects should be lying down for at least 10 minutes prior to each 12-lead ECG. The Investigator may perform additional ECGs for safety at other times if deemed necessary.

Pulmonary Function Tests (PFT)

PFTs to be evaluated are the forced expiratory volume in 1 second (FEV1), and the forced expiratory vital capacity (FVC), and the diffusing capacity of the lungs for carbon monoxide (DLCO). DLCO will be performed at sites where equipment is available. The screening PFTs must be done at least 8 days prior to Day 1. If a subject's PFTs meet the exclusion criteria due to quality issues, the PFTs may be repeated once during the Screening period.

Ophthalmological Examinations

Optical coherence tomography (OCT) will be performed to determine the presence of macular oedema.

Progressive Multifocal Leukoencephalopathy (PML) Checklist

Subjects will be monitored at each visit for the presence of signs or symptoms of PML using the PML Checklist. The PML subjective checklist will be administered at each visit by the Investigator, or appropriate designee, and whenever the subject or his/her family member reports the symptom. When a positive subjective checklist is confirmed, the IMP dose will be interrupted and an objective checklist will be performed by the Investigator. Only the portion of the objective checklist that corresponds to the portion of the positive subjective checklist will be performed. IMP dose may be re-started based on the Investigator's assessment of the severity of the symptoms.

Clinical Laboratory Tests

Blood draws will be collected in a fasting (8 hours) state. Laboratory safety tests may be performed at various unscheduled time points, if deemed necessary by the Investigator or designee. Details on collection, preparation and shipping of blood and urine samples are provided in the Laboratory Manual.

In addition to the lab test specified in Table 3, stool samples will be collected for microbiology testing and for fecal UC-related biomarker testing (calprotectin and lactoferrin). Details on collection, preparation and shipping of stool samples are provided in the Laboratory Manual.

TABLE 3

Clinical Laboratory Tests

| | |
|---|---|
| Hematology | Serum Chemistry[2] |
| Hemoglobin | Blood Urea Nitrogen |
| Hematocrit | Bilirubin (total and direct) |
| Total and differential leukocyte count[1] | Alkaline phosphatase |
| Red blood cell count | Aspartate aminotransferase |
| Platelet count | Alanine aminotransferase |
| Coagulation | Albumin |
| Prothrombin time/international | Sodium |
| normalized ratio | Potassium |
| Activated partial thromboplastin time | Magnesium |
| Serum C-Reactive Protein (CRP) | Calcium |
| Urinalysis | Chloride |
| pH | Glucose |
| Specific gravity | Creatine kinase |
| Protein[4] | Creatinine[3] |
| Glucose | Lipid Panel: |
| Ketones | Total cholesterol |
| Bilirubin | HDL |
| Blood[4] | LDL |
| Nitrite[4] | Triglycerides |
| Urobilinogen | Additional Tests |
| Leukocyte esterase[4] | HIV test |
| | HBsAg |
| | HBcAb |
| | HBsAb |
| | HCV RNA |
| | SARS-CoV-2 screen |
| | Urine drug screen: |
| | Opiates |
| | Opioids |
| | Amphetamines |
| | Cocaine |
| | Cannabinoids |
| | Urine alcohol screen |
| | Urine cotinine |
| | Serum pregnancy test (for WOCBP only) |
| | HbA1c |

[1]WBC and absolute neutrophil count (ANC) will be provided to the Investigator. All other WBC differential values, absolute and percent, including lymphocyte count results (absolute, percent, and subsets) will remain blinded throughout the Double-Blind Period. Lymphocyte count will be available only to the unblinded reviewer.

[2]Serum chemistry tests will be performed after at least an 8-hour fast.

[3]At Screening, creatinine clearance will be calculated using the Cockcroft-Gault formula.

[4]If urinalysis is positive for protein, blood, nitrite and/or leukocyte esterase, a microscopic examination (for red blood cells, white blood cells, bacteria, casts, and epithelial cells) will be performed.

Pharmacokinetics (PK) and Pharmacodynamics (PD) Variables

All subjects in the Double-Blind Period will have pre-dose (within 1 hour) PK samples collected on Days 1, 15, 29, 57, 85, and 169/EOS. In the OLE Period, all subjects will have pre-dose (within 1 hour) PK samples collected on Days 99, 113, 169, 225, 281, 337, and 421.

A subset of approximately 20 subjects in each treatment group will undergo serial PK sampling on Day 1 and Day 85. Blood samples will be collected within 1 hour before (pre-dose) and 1, 2, 4, 6, 8, 10, 12, and 24 hours after dosing.

Windows for blood sample collection are ±5 min for the first 2 hours, ±30 min from the 4-hour to 12-hour timepoints, and ±2 hours from the 24-hour timepoint. The window for pre-dose sample collection is 1 hour. Instructions for collection, preparation, labeling and shipping of PK samples are provided in the Laboratory Manual.

In addition to the PK sample collections outlined above, a PK sample collection will be obtained if a cardiac-related SAE occurs. If the subject is discontinued from further treatment, an additional blood sample for PK analysis will be collected within 3 days of the subject's last dose.

Total lymphocyte count and change from Baseline in lymphocyte count will be assessed for the PD properties of amiselimod and MT-1303-P. Blood samples for lymphocyte counts should be collected prior to study drug administration. Lymphocyte counts obtained from the clinical laboratory tests will be sent to the independent, unblinded, qualified medical professional for review as.

Exploratory PD Variable

Lymphocyte subset count and change from Baseline for each lymphocyte subset will be assessed. A separate blood sample for lymphocyte subset assessment will be collected at all visits except Screening. The blood sample for lymphocyte subset counts should be collected prior to study drug administration. Lymphocyte subsets include the following panels: (1) T, B and natural killer cells and (2) T cell subset.

Concomitant Medications and Procedures

Concomitant Medications

A concomitant medication is any drug or substance administered between the signing of the informed consent and the EOS (end of study) Visit.

Enrollment in any other drug, biologic, or device clinical study or treatment with an approved therapy for investigational development or unapproved investigational drug under development is not allowed.

Adverse events related to administration of concomitant medication must be documented in the appropriate eCRF.

If subjects are receiving the following UC treatments, they must be on a stable dose for at least 28 days prior to randomization and remain at that stable dose throughout the study:

Oral or rectal 5-ASAs,

Oral corticosteroids (≤20 mg prednisolone equivalent).

Prohibited Medications

Subjects taking prohibited medications during the study will be discontinued. Protocol deviations for prohibited medication will not be considered. Treatment with the following products is not allowed during the study:

Use of any other sphingosine 1-phosphate (S1P) receptor modulators (including fingolimod, ozanimod, and etrasimod).

Use of oral or rectal 5-ASAs (e.g., mesalamine, sulfasalazine, olsalazine, or balsalazide) on an unstable dose.

Initiation of treatment with an oral corticosteroid or change in the stable dose (≤20 mg prednisolone equivalent) of oral corticosteroids assessed at Screening Visit.

Use of non-oral (IV or rectal) corticosteroid.

Use of immunosuppressants (e.g., AZA, 6-MP, or MTX).

Use of cyclosporine, mycophenolate mofetil, or thalidomide.

Use of tacrolimus.

Use of intravenous immunoglobulin, plasmapheresis, or cytapheresis therapy.

Use of any biologics or newly approved UC treatment agents (e.g., infliximab, adalimumab, certolizumab, golimumab, etanercept, vedolizumab, ustekinumab, tofacitinib, or natalizumab).

Use of Class I or Class III anti-arrhythmic drugs, calcium-channel blockers, β-blockers, or drugs that prolong the QT interval.

Concomitant Procedures

A concomitant procedure is any therapeutic intervention (e.g., surgery/biopsy, physical therapy) or diagnostic assessment (e.g., blood gas measurement, bacterial cultures) performed between the time the subject is enrolled in the study and the EOS or EOT Visit.

The use of concomitant therapies or procedures must be recorded on the subject's eCRF, according to instructions for eCRF completion. Adverse events related to administration of these therapies or procedures must be documented in the appropriate eCRF.

Continuation of Treatment

Subjects who complete the Day 85 Visit will be given the opportunity to continue into the OLE Period, if eligible, to receive active amiselimod for up to one year. Subjects that cannot tolerate the IMP, are not eligible, or choose to not continue into the OLE Period will not continue to receive IMP and will return to the clinic for a Safety Follow-up Visit on Day 169, 84 days [12 weeks] after completion of IMP treatment.

Subjects that do continue into the OLE Period will receive treatment with IMP for up to one year (48 weeks) after which treatment with amiselimod will cease.

The terms and expressions employed herein are used as terms of description and not of limitation, and there is no intention in the use of such terms and expressions of excluding any equivalents of the features shown and described or portions thereof, but it is recognized that various modifications are possible within the scope of the embodiments described herein. Thus, it should be understood that although the disclosure herein includes specific embodiments and optional features, modification and variation of the compositions, methods, and concepts herein disclosed may be resorted to by those of ordinary skill in the art, and that such modifications and variations are considered to be within the scope of embodiments of the disclosure.

What is claimed is:

1. A method of treating or ameliorating ulcerative colitis in a subject in need thereof, the method comprising:

administering to the subject a first therapeutically effective dose of amiselimod, or a pharmaceutically acceptable salt or enantiomer thereof, during a first administration period; and administering to the subject a second therapeutically effective dose of amiselimod, or a pharmaceutically acceptable salt or enantiomer thereof, during a second administration period, wherein the first therapeutically effective dose is about 1.5 to about 2.5 times larger than the second therapeutically effective dose.

2. The method of claim 1, wherein administering the first dose to the subject does not induce a negative chronotropic effect in heart rate in the subject.

3. The method of claim 1, wherein the first dose is about 2 times larger than the second dose.

4. The method of claim 1, wherein at least one of the first dose and the second dose is a daily dose.

5. The method of claim 1, wherein the first dose and the second dose are each independently about 0.05 mg to about 10 mg.

6. The method of claim 1, wherein the first dose and second dose are each independently about 0.1 mg to about 1 mg.

7. The method of claim 1, wherein the first dose is about 0.1, 0.2, 0.3, 0.4, 0.5, 0.6, 0.7, 0.8, 0.9, or about 1.0 mg.

8. The method of claim 1, wherein the first dose is about 0.8 mg or about 0.4 mg.

9. The method of claim 1, wherein the first administration period is 1 to 21 days.

10. The method of claim 1, wherein the first administration period is 1 to 14 days.

11. The method of claim 1, wherein the first administration period is at least 11 days.

12. The method of claim 1, wherein the second administration period is at least 1 year.

13. The method of claim 1, further comprising administering to the subject at least one additional therapeutic agent that treats or ameliorates ulcerative colitis.

14. A method of reducing inflammation in a subject's gastrointestinal (GI) tract, the method comprising:

administering to the subject a first therapeutically effective dose of amiselimod, or a pharmaceutically acceptable salt or enantiomer thereof, during a first administration period; and administering to the subject a second therapeutically effective dose of amiselimod, or a pharmaceutically acceptable salt or enantiomer thereof, during a second administration period, wherein the first therapeutically effective dose is about 1.5 to about 2.5 times larger than the second therapeutically effective dose.

15. The method of claim 14, wherein administering the first dose to the subject does not induce a negative chronotropic effect in heart rate in the subject.

16. The method of claim 14, wherein the first dose is about 2 times larger than the second dose.

17. The method of claim 14, wherein at least one of the first dose and the second dose is a daily dose.

18. The method of claim 14, wherein the first dose and the second dose are each independently about 0.05 mg to about 10 mg.

19. The method of claim 14, wherein the first dose is about 0.1, 0.2, 0.3, 0.4, 0.5, 0.6, 0.7, 0.8, 0.9, or about 1.0 mg.

20. The method of claim 14, wherein the first dose is about 0.8 mg or about 0.4 mg.

21. The method of claim 14, wherein the first administration period is 1 to 14 days.

22. The method of claim 14, wherein the second administration period is at least 1 year.

23. The method of claim 14, further comprising administering to the subject at least one additional therapeutic agent that treats or ameliorates ulcerative colitis.

24. A method of treating mild to moderate ulcerative colitis in a subject in need thereof, the method comprising:

administering to the subject a first therapeutically effective dose of amiselimod, or a pharmaceutically acceptable salt or enantiomer thereof, during a first administration period; and administering to the subject a second therapeutically effective dose of amiselimod, or a pharmaceutically acceptable salt or enantiomer thereof, during a second administration period, wherein the first therapeutically effective dose is about 1.5 to about 2.5 times larger than the second therapeutically effective dose.

25. The method of claim 24, wherein administering the first dose to the subject does not induce a negative chronotropic effect in heart rate in the subject.

26. The method of claim 24, wherein the first dose is about 2 times larger than the second dose.

27. The method of claim 24, wherein at least one of the first dose and the second dose is a daily dose.

28. The method of claim 24, wherein the first dose and the second dose are each independently about 0.05 mg to about 10 mg.

29. The method of claim 24, wherein the first dose and second dose are each independently about 0.1 mg to about 1 mg.

30. The method of claim 24, wherein the first dose is about 0.1, 0.2, 0.3, 0.4, 0.5, 0.6, 0.7, 0.8, 0.9, or about 1.0 mg.

31. The method of claim 24, wherein the first dose is about 0.8 mg or about 0.4 mg.

32. The method of claim 24, wherein the first administration period is 1 to 21 days.

33. The method of claim 24, wherein the first administration period is 1 to 14 days.

34. The method of claim 24, wherein the first administration period is at least 11 days.

35. The method of claim 24, wherein the first administration period is 1 to 14 days.

36. The method of claim 24, further comprising administering to the subject at least one additional therapeutic agent that treats or ameliorates ulcerative colitis.

37. The method of claim 24, wherein the first dose is administered once a day (QD), twice a day (BID), three times a day (TID), or four times a day (QID), optionally wherein the first dose is administered once a day (QD).

38. The method of claim 24, wherein the second dose is administered once a day (QD), twice a day (BID), three times a day (TID), or four times a day (QID), optionally wherein the first dose is administered once a day (QD).

39. The method of claim 37, wherein one of the following applies:

(a) the second dose is administered QD, BID, TID, or QID every other day during the second administration period;

(b) the second dose is administered QD, BID, TID, or QID every two days during the second administration period;

(c) the second dose is administered QD, BID, TID, or QID every three days during the second administration period;

(d) the second dose is administered QD, BID, TID, or QID every four days during the second administration period;

(e) the second dose is administered QD, BID, TID, or QID every five days during the second administration period;

(f) the second dose is administered QD, BID, TID, or QID every six days during the second administration period;

(g) the second dose is administered QD, BID, TID, or QID every seven during the second administration period.

* * * * *